US009826949B2

(12) United States Patent
Ning et al.

(10) Patent No.: US 9,826,949 B2
(45) Date of Patent: Nov. 28, 2017

(54) METHODS AND APPARATUS FOR DIFFERENTIAL PHASE-CONTRAST CONE-BEAM CT AND HYBRID CONE-BEAM CT

(71) Applicant: University of Rochester, Rochester, NY (US)

(72) Inventors: Ruola Ning, Rochester, NY (US); Weixing Cai, Rochester, NY (US)

(73) Assignee: University of Rochester, Rochester, NY (US)

( * ) Notice: Subject to any disclaimer, the term of this patent is extended or adjusted under 35 U.S.C. 154(b) by 33 days.

(21) Appl. No.: 14/383,087

(22) PCT Filed: Mar. 5, 2013

(86) PCT No.: PCT/US2013/029137
§ 371 (c)(1),
(2) Date: Sep. 4, 2014

(87) PCT Pub. No.: WO2014/137325
PCT Pub. Date: Sep. 12, 2014

(65) Prior Publication Data
US 2016/0022235 A1    Jan. 28, 2016

Related U.S. Application Data

(60) Provisional application No. 61/606,562, filed on Mar. 5, 2012.

(51) Int. Cl.
*A61B 6/03*    (2006.01)
*A61B 6/00*    (2006.01)
*G06T 11/00*   (2006.01)

(52) U.S. Cl.
CPC ............... *A61B 6/484* (2013.01); *A61B 6/03* (2013.01); *A61B 6/032* (2013.01); *A61B 6/4085* (2013.01);
(Continued)

(58) Field of Classification Search
CPC ..... A61B 6/032; A61B 6/4035; A61B 6/4085; A61B 6/4291; A61B 6/484; A61B 6/502
(Continued)

(56) References Cited

U.S. PATENT DOCUMENTS

| 5,999,587 A | 12/1999 | Ning et al. |
| 6,075,836 A | 6/2000 | Ning |

(Continued)

FOREIGN PATENT DOCUMENTS

| WO | WO 2011-070521 | 6/2011 |
| WO | 2012164092 | 12/2012 |
| WO | WO 2012-164092 | 12/2012 |

OTHER PUBLICATIONS

International Preliminary Report on Patentability dated Sep. 8, 2015.
(Continued)

*Primary Examiner* — Allen C. Ho
(74) *Attorney, Agent, or Firm* — Cooper & Dunham LLP

(57) ABSTRACT

A raw DPC (differential phase contrast) image of an object is acquired. The background phase distribution due to the non-uniformity of the grating system is acquired by the same process without an object in place, and the true DPC image of the object is acquired by subtracting the background phase distribution from the raw DPC image.

52 Claims, 12 Drawing Sheets

(52) U.S. Cl.
CPC ............ *A61B 6/4291* (2013.01); *A61B 6/466* (2013.01); *A61B 6/502* (2013.01); *A61B 6/5205* (2013.01); *G06T 11/006* (2013.01); *A61B 6/4035* (2013.01)

(58) Field of Classification Search
USPC .................................. 378/16, 19, 36, 37, 62
See application file for complete search history.

(56) References Cited

U.S. PATENT DOCUMENTS

| | | | | |
|---|---|---|---|---|
| 6,298,110 | B1 | 10/2001 | Ning | |
| 6,477,221 | B1 | 11/2002 | Ning | |
| 6,480,565 | B1 | 11/2002 | Ning | |
| 6,504,892 | B1 | 1/2003 | Ning | |
| 6,618,466 | B1 | 9/2003 | Ning | |
| 6,987,831 | B2 | 1/2006 | Ning | |
| 7,433,444 | B2* | 10/2008 | Baumann | A61B 6/032 378/145 |
| 7,440,542 | B2* | 10/2008 | Baumann | A61B 6/484 378/44 |
| 7,453,981 | B2* | 11/2008 | Baumann | A61B 6/484 378/21 |
| 7,486,770 | B2* | 2/2009 | Baumann | A61B 6/032 378/145 |
| 7,492,871 | B2* | 2/2009 | Popescu | A61B 6/00 378/145 |
| 7,522,698 | B2* | 4/2009 | Popescu | A61B 6/032 378/19 |
| 7,522,708 | B2* | 4/2009 | Heismann | A61B 6/00 378/145 |
| 7,532,704 | B2* | 5/2009 | Hempel | A61B 6/032 378/145 |
| 7,564,941 | B2* | 7/2009 | Baumann | A61B 6/484 378/146 |
| 7,639,786 | B2* | 12/2009 | Baumann | A61B 6/484 378/145 |
| 7,646,843 | B2* | 1/2010 | Popescu | A61B 6/032 356/521 |
| 7,693,256 | B2 | 4/2010 | Brahme et al. | |
| 7,817,777 | B2* | 10/2010 | Baumann | A61B 6/00 378/36 |
| 7,889,838 | B2* | 2/2011 | David | A61B 6/4233 378/36 |
| 7,924,973 | B2* | 4/2011 | Kottler | G01B 15/025 378/36 |
| 7,945,018 | B2* | 5/2011 | Heismann | A61B 6/032 378/145 |
| 7,949,095 | B2* | 5/2011 | Ning | A61B 6/032 378/4 |
| 7,983,381 | B2* | 7/2011 | David | A61B 6/032 378/4 |
| 8,005,185 | B2* | 8/2011 | Popescu | A61B 6/06 378/19 |
| 8,009,796 | B2* | 8/2011 | Popescu | A61B 6/032 378/19 |
| 8,041,004 | B2* | 10/2011 | David | A61B 6/484 378/36 |
| 8,073,099 | B2* | 12/2011 | Niu | A61B 6/00 378/36 |
| 8,165,270 | B2* | 4/2012 | David | G01T 1/00 378/145 |
| 8,184,771 | B2* | 5/2012 | Murakoshi | G01N 23/20075 378/145 |
| 8,223,924 | B2* | 7/2012 | Borner | A61B 6/032 378/145 |
| 8,233,587 | B2* | 7/2012 | Sato | G21K 1/06 378/36 |
| 8,243,879 | B2* | 8/2012 | Itoh | G21K 1/025 359/238 |
| 8,351,570 | B2* | 1/2013 | Nakamura | G21K 1/06 378/145 |
| 8,374,309 | B2* | 2/2013 | Donath | A61B 6/032 378/145 |
| 8,411,816 | B2* | 4/2013 | Ohara | A61B 6/484 378/36 |
| 8,451,975 | B2* | 5/2013 | Tada | A61B 6/4291 378/207 |
| 8,515,002 | B2* | 8/2013 | Huang | B82Y 10/00 378/6 |
| 8,565,371 | B2* | 10/2013 | Bredno | A61B 6/032 378/9 |
| 8,591,108 | B2* | 11/2013 | Tada | A61B 6/00 378/207 |
| 8,632,247 | B2* | 1/2014 | Ishii | A61B 6/00 378/207 |
| 8,737,561 | B2* | 5/2014 | Sato | B26D 3/06 378/149 |
| 8,755,487 | B2* | 6/2014 | Kaneko | A61B 6/06 378/36 |
| 8,767,916 | B2* | 7/2014 | Hashimoto | A61B 6/484 378/62 |
| 8,781,069 | B2* | 7/2014 | Murakoshi | A61B 6/4233 378/36 |
| 8,831,174 | B2* | 9/2014 | Kohara | A61B 6/06 378/62 |
| 8,848,863 | B2* | 9/2014 | Schusser | G21K 1/06 378/16 |
| 8,855,265 | B2* | 10/2014 | Engel | A61B 6/00 378/36 |
| 8,913,714 | B2* | 12/2014 | Michel | G01N 23/20075 250/370.09 |
| 8,989,347 | B2* | 3/2015 | Sperl | G01N 23/046 250/370.08 |
| 8,989,353 | B2* | 3/2015 | Kaneko | G21K 1/025 378/145 |
| 9,001,967 | B2* | 4/2015 | Baturin | A61B 6/484 378/156 |
| 9,001,969 | B2* | 4/2015 | Murakoshi | A61B 6/4233 378/70 |
| 9,014,333 | B2* | 4/2015 | Sperl | A61B 6/484 378/132 |
| 9,025,726 | B2* | 5/2015 | Ishii | A61B 6/484 378/62 |
| 9,036,773 | B2* | 5/2015 | David | A61B 6/4035 378/36 |
| 9,063,055 | B2* | 6/2015 | Ouchi | G01N 23/04 |
| 9,066,649 | B2* | 6/2015 | Roessl | A61B 6/00 |
| 9,084,528 | B2* | 7/2015 | Geller | A61B 6/00 |
| 9,105,369 | B2* | 8/2015 | Koehler | A61B 6/032 |
| 9,117,296 | B2* | 8/2015 | Stampanoni | A61B 6/483 |
| 9,123,451 | B2* | 9/2015 | Nagai | G21K 1/06 |
| 9,134,259 | B2* | 9/2015 | Huang | A61B 6/484 |
| 9,239,304 | B2* | 1/2016 | Yamaguchi | A61B 6/00 |
| 9,269,471 | B2* | 2/2016 | Roessl | A61B 6/484 |
| 9,287,017 | B2* | 3/2016 | Koehler | G21K 1/06 |
| 9,329,141 | B2* | 5/2016 | Stutman | G01N 23/046 |
| 9,330,456 | B2* | 5/2016 | Sperl | G06T 7/0012 |
| 9,348,067 | B2* | 5/2016 | Vogtmeier | G02B 5/1857 |
| 9,357,975 | B2* | 6/2016 | Baturin | G01N 23/20075 |
| 9,364,191 | B2* | 6/2016 | Ning | A61B 6/4241 |
| 2009/0092227 | A1 | 4/2009 | David et al. | |
| 2009/0238334 | A1 | 9/2009 | Brahme et al. | |
| 2010/0220832 | A1 | 9/2010 | Ning et al. | |
| 2010/0246764 | A1 | 9/2010 | Itoh et al. | |
| 2011/0293064 | A1 | 12/2011 | Huang et al. | |
| 2012/0008747 | A1 | 1/2012 | Roessi et al. | |
| 2013/0094625 | A1* | 4/2013 | Huang | A61B 6/484 378/6 |

OTHER PUBLICATIONS

Written Opinion of the International Searching Authority dated Dec. 10, 2013.

Dec. 10, 2013 International Search Report and Written Opinion in connection with corresponding International Application No. PCT/US2013/029137.

(56) References Cited

OTHER PUBLICATIONS

T Weitkamp, A Diaz, C David, F Pfeiffer, M Stampanoni, P Cloetens and E Ziegler, "X-ray phase imaging with a grating interferometer," Opt. Express 2005; 13(16):6296-6304.

G. Faris and R. Byer, "Three-dimensional beam-deflection optical tomography of a supersonic jet," Appl. Opt. 27(24), 5202-5212 (1988).

A. Momose, W. Yashiro, S. Harasse, H. Kuwabara, K. Kawabata, "Four-dimensional x-ray phase tomography with Talbot interferometer and white synchrotron light," Proc. SPIE 7804, 780405 (2010).

D. Donoho, "Compressed sensing," IEEE Trans Information Theory 52(4), 1289-1306 (2006).

Oct. 16, 2015 Supplemental European International Search Report in connection with corresponding International Application No. PCT/US2013/029137.

\* cited by examiner

TYPICAL RECONSTRUCTION SLICES OF A CYLINDER PHANTOM. (a) AND (c) USE DPC IMAGES RETRIEVED FROM MOIRÉ PATTER-BASED APPROACH. FOR COMPARISON, (b) AND (d) USE DPC IMAGES RETRIEVED FORM PHASE STEPPING APPROACH. THE RESULTING RECONSTRUCTION IMAGES ARE COMPARABLE USING THESE TWO METHODS.

METHODS AND APPARATUS FOR DIFFERENTIAL PHASE-CONTRAST CONE-BEAM CT AND HYBRID CONE-BEAM CT

CROSS-REFERENCE TO RELATED APPLICATIONS

This present application is a §371 national stage of PCT International Application No. PCT/US2013029137, filed Mar. 5, 2013, claiming priority of U.S. Provisional Patent Application No. 61/606,562, filed Mar. 5, 2012, the contents of each of which are hereby incorporated by reference in their entirety.

STATEMENT OF GOVERNMENT INTEREST

This invention was made with government support under Grant No. R01 CA 143050 awarded by National Institutes of Health. The government has certain rights in the invention.

FIELD OF THE INVENTION

The present invention is directed to cone-beam computed tomography (CT) imaging and more particularly to phase-contrast cone-beam CT for such uses as breast imaging.

DESCRIPTION OF RELATED ART

According to the National Cancer Institute, one out of eight women will be diagnosed with breast cancer in their lifetime. And while a reduction in mortality from breast cancer is evident in published reports, each year 40,000 women will die of the disease.

The optimal breast imaging technique detects tumor masses when they are small, preferably less than 10 mm in diameter. It is reported that women with mammographically detected invasive breast carcinoma 1-10 mm in size have a 93% 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Although mammography, which on average can detect cancers ~12 mm in size, is the most effective tool for the early detection of breast cancer currently available mammography has relatively low sensitivity to small breast cancers (under several millimeters). Specificity and the positive predictive value of mammography remain limited owing to structure and tissue overlap. Limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers. The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large scale clinical trial, the Digital Mammographic Imaging Screening Trial (DMIST), showed that the rates of false positives for DM and SFM were the same.

The relatively low specificity of mammography leads to biopsy for indeterminate cases despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

To address the mammography limitations as indicated above, we have previously developed a cone beam breast CT (CBBCT). Briefly, the major features of the prototype include a horizontal, ergonomically designed patient table with a modular insert to optimize coverage of the uncompressed breast, including the chest wall; wide openings (1 m) on each side of the patient table for easy access to the breast for positioning and potentially good access for imaging-guided biopsy and other procedures without significantly changing the basic platform; and slip-ring technology that facilitates efficient dynamic contrast imaging studies and angiogenesis imaging in the future.

The results of phantom studies indicate that CBBCT can achieve a spatial resolution up to ~2.8 lp/mm, allowing detection of a 2 mm carcinoma and the microcalcifications ~0.2 mm in size for an average size breast (~13 cm in diameter at the chest wall) with a total dose of ~5 mGy. This dose is less than that of a single mammography exam, assuming two views are required for each breast. The image quality of CBBCT for visualizing breast tissues, breast tumors and calcifications is excellent, and coverage of the breast, including the chest wall region, is at least equivalent to mammography. Visualization of major blood vessels is very good without using a contrast agent.

Ultrasound (US) is used diagnostically to distinguish fluid versus solid masses and for localization and biopsy. Lately, it has been investigated with some success to determine benign versus malignant masses through a US exam. US is a low spatial resolution study, has severe limitations in visualizing and characterizing calcifications and is highly dependent on operator skill.

Intravenous dynamic contrast enhanced breast MRI (CEBMRI) currently is the only tool that provides functional information to aid in the diagnosis of breast cancer. The CEBMRI study has a high negative predictive value and near 100% sensitivity for invasive breast cancer and serves as a valuable adjunctive modality in managing the breast cancer patient once cancer has been diagnosed by other means. Because it is a tomographic study, it is currently the only breast imaging modality that is FDA approved and can truly be compared to CBBCT. CEBMRI is fully dependent on contrast resolution arising from intravenous contrast agents and the neovasculature associated with tumors. The difference in CEBMRI and all other imaging is that the image reflects contrast enhancement of vasculature rather than the actual breast anatomy. Although CEBMRI has a high sensitivity for invasive cancers, current techniques may be limited in detecting ductal carcinoma in situ (DCIS). CEBMRI is not able to distinguish calcifications and the proposed non-neovasculature involvement with DCIS, which are evident in up to 50% of breast cancers not associated with a mass.

Digital breast tomosynthesis (DBT) presently under development aims to mitigate the effect of overlapping structures. Though a measure of success has been achieved, DBT is fundamentally limited by its constraints in projection geometry; the tomographic slice is not well defined, which can cause a loss of resolution in the axial direction that affects visualization of subtle features, such as amorphous microcalcifications. CBBCT can provide isotropic high-resolution imaging of the entire breast in a more complete tomographic approach compared to other modalities, with without breast compression. It is likely to be of particular value for imaging dense breasts and breasts with implants.

As discussed above, compared to mammography including digital mammography, CBBCT has made significant advancements in detecting breast cancer. However, to accurately characterize breast tumors and calcifications and significantly reduce the biopsy rate and false positive rate of breast biopsy, it is desirable that the CBBCT should achieve a comparable spatial resolution of the pathology image which is the gold standard for breast cancer diagnosis. The requirement of multifold increase in spatial resolution will mandate increasing the radiation dose over 100 times in order to maintain the same contrast-to-noise ratio (CNR) as current CBBCT. For example, if the spatial resolution is required to be increased from 2 lp/mm to 25 lp/mm, to maintain a clinical acceptable CNR, the dose level would be increased from ~6 mGy for an average sized breast with the current CBBCT ~186 times to 1.1 Gy. This dose increase is clinically prohibited.

The following references are considered to provide background information:
1. T. Weitkamp, A. Diaz, C. David, F. Pfeiffer, M. Stampanoni, P. Cloetens and E. Ziegler, "X-ray phase imaging with a grating interferometer," Opt. Express 2005; 13(16): 6296-6304.
2. G. Faris and R. Byer, "Three-dimensional beam-deflection optical tomography of a supersonic jet," Appl. Opt. 27(24), 5202-5212 (1988).
3. A. Momose, W. Yashiro, S. Harasse, H. Kuwabara, K. Kawabata, "Four-dimensional x-ray phase tomography with Talbot interferometer and white synchrotron light," Proc. SPIE 7804, 780405 (2010).
4. D. Donoho, "Compressed sensing," IEEE Trans Information Theory 52(4), 1289-1306 (2006)

SUMMARY OF THE INVENTION

It is therefore an object of the invention to allow an increase in spatial resolution without increasing the dose to a prohibited level.

It is therefore another object of the invention to allow substantially reduced x-ray radiation dose to a patient without reducing spatial resolution and contrast to noise ratio.

It is therefore another object of the invention to allow mechanically rigid and robust implementation for a rotational-gantry system of phase contrast cone beam CT.

It is therefore another object of the invention to allow substantially reduce x-ray radiation dose to a patient for grating-based phase contrast cone beam CT imaging.

To achieve the above and other objects, the present invention is directed to a system and method for breast imaging or other purposes (for example, vascular imaging, pediatric cone beam CT, whole body CT imaging and interventional cone beam CT), using x-ray differential phase-contrast cone beam CT. X-ray phase contrast cone beam CT and cone beam CT imaging as an emerging new technology will potentially achieve the spatial resolution level up to 25 lp/mm (20 μm voxel size) while maintaining an x-ray dose similar to that of the current CBBCT and mammography. In addition, since x-ray phase contrast imaging is dependent on the principles of refraction and interference of x-ray waves, more subtle information can be detected by retrieving the phase coefficients than that possible with conventional attenuation-based x-ray imaging techniques retrieving attenuation coefficients.

Conventional attenuation-based CT and cone beam CT are quite efficient in distinguishing absorption contrast between soft and hard tissues that have very different linear attenuation coefficients. However, when imaging soft tissues including breast tissues, the low absorption contrast differences of the breast structures (benign and malignant) limit its performance. Phase-contrast techniques are expected to provide an alternative way for soft tissue imaging. Unlike the principle of absorption contrast, phase-contrast imaging originates from the wave nature of x-rays, where refraction and diffraction need to be considered. As an electromagnetic wave, the x-ray is usually characterized by its wavelength, amplitude and phase. When it goes through a medium, its amplitude is attenuated, and its phase is shifted. In x-ray technology, the refraction index n of a material is usually expressed as a complex number $n=1-\delta+i\beta$. The imaginary part $\beta$ contributes to the attenuation of the amplitude, and the real part $\delta$ is responsible for the phase shift. It has been shown theoretically and experimentally that $\delta$ is usually more than $10^3$ times larger than $\beta$. Therefore, a phase contrast imaging technique will potentially provide 1000 times higher object contrast than attenuation-based CT and cone beam CT techniques.

In the past decade, various phase-contrast techniques have been developed to manifest the contrast of $\delta$, almost all of which depend on micro-focus x-ray tubes or synchrotron radiation that are not practical for widespread clinical applications. Recently, a new phase contrast imaging technique called the differential phase-contrast (DPC) technique has been proposed, which is a grating-based interferometry method. A high power hospital-grade x-ray tube with a wide polychromatic spectrum and high output x-ray power can be used to acquire DPC images. However, it has not previously been used in the context of the present invention.

Related systems and methods are disclosed in the following U.S. patents: U.S. Pat. No. 7,949,095, "Method and apparatus of differential phase-contrast fan beam CT, cone beam CT and hybrid cone beam CT"; U.S. Pat. No. 6,987,831,"Apparatus and method for cone beam volume computed tomography breast imaging"; U.S. Pat. No. 6,618,466, "Apparatus and method for x-ray scatter reduction and correction for fan beam CT and cone beam volume CT"; U.S. Pat. No. 6,504,892, "System and method for cone beam volume computed tomography using circle-plus-multiple-arc orbit"; U.S. Pat. No. 6,480,565 "Apparatus and method for cone beam volume computed tomography breast imaging"; U.S. Pat. No. 6,477,221, "System and method for fast parallel cone beam reconstruction using one or more microprocessors"; U.S. Pat. No. 6,298,110, "Cone beam volume CT angiography imaging system and method"; U.S. Pat. No. 6,075,836, "Method of and system for intravenous volume tomographic digital angiography imaging"; and U.S. Pat. No. 5,999,587, "Method of and system for cone-beam tomography reconstruction," whose disclosures are all incorporated by reference in their entireties into the present disclosure. The techniques disclosed in those patents can be used in conjunction with the techniques disclosed herein.

BRIEF DESCRIPTION OF THE DRAWINGS

Preferred embodiments of the present invention will be set forth in detail with reference to the drawings, in which.

DETAILED DESCRIPTION OF THE PREFERRED EMBODIMENTS

Figure 1A:
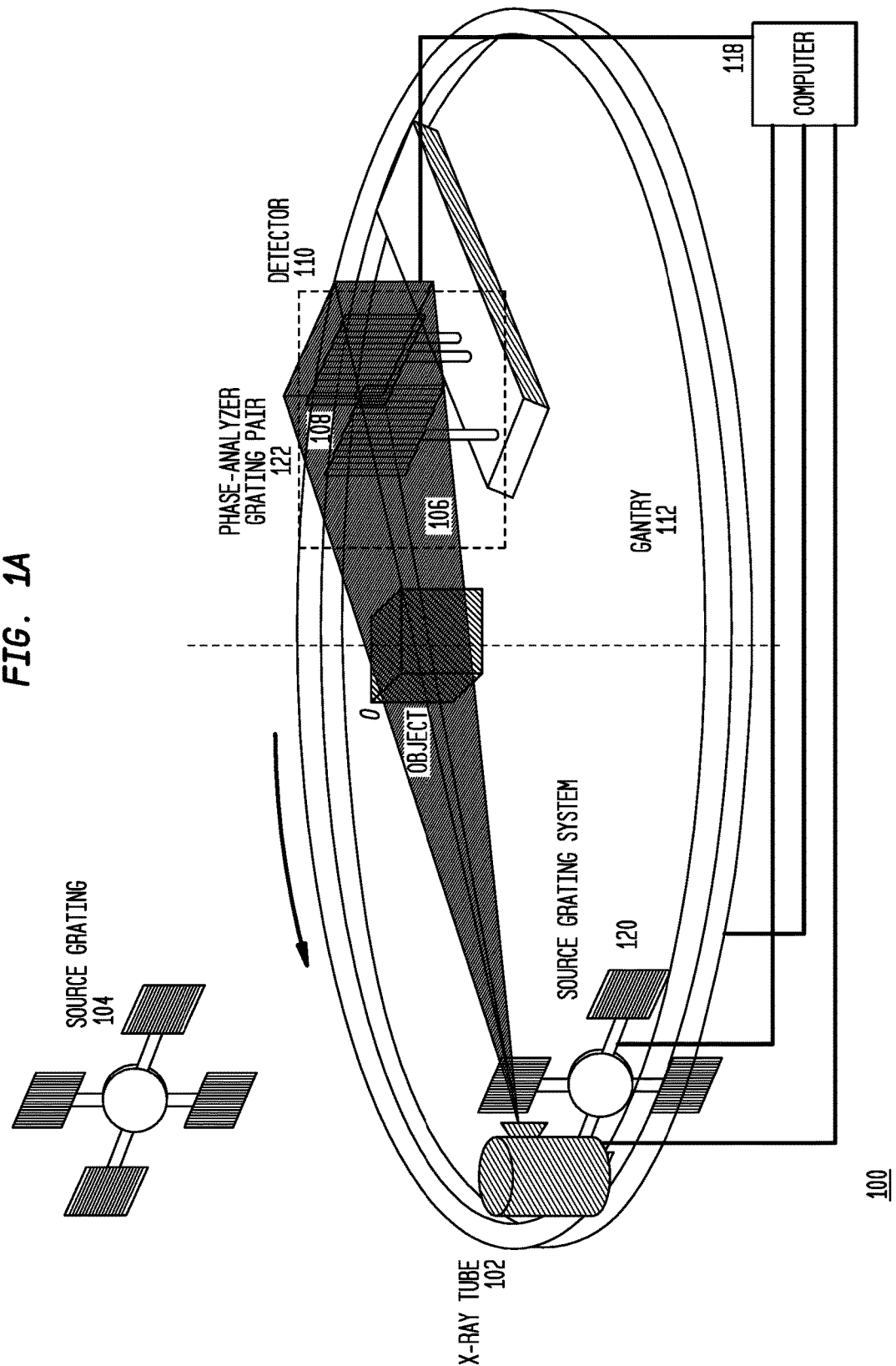
FIGS. 1A and 1B are schematic diagrams showing a system according to a first preferred embodiment.

Preferred embodiments of the present invention will be set forth in detail with reference to the drawings, in which like reference numerals refer to like elements or steps throughout.

Figure 1B:
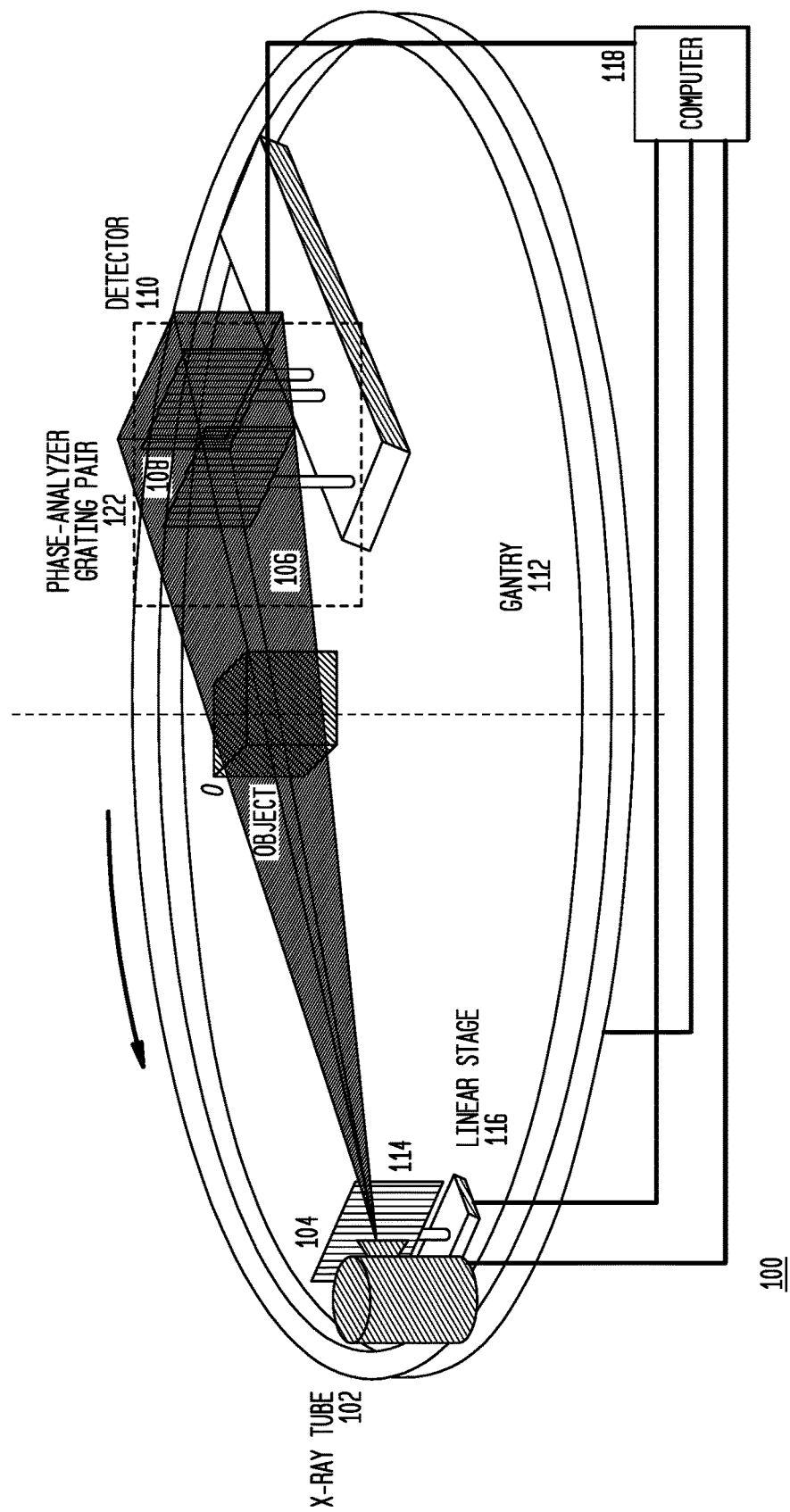

A first preferred embodiment is directed to a differential phase-contrast cone-beam CT system (DPC-CBCT) for in vivo clinical imaging using the differential phase-contrast imaging technique. As shown in FIGS. 1A and 1B, such a DPC-CBCT system 100 includes a hospital-grade x-ray tube 102 with a source grating 104, a high-resolution detector 110 and a phase-analyzer grating pair 122 mounted on a gantry 112. To ensure the mechanical precision and stability, the source grating 104 will be stepped to improve mechanical tolerance. The stepping mechanism of the source grating 104 can be designed either as the dial source grating system 120 in FIG. 1A or as the linear stage-based mechanism in FIG. 1B. The purpose of the source grating system 120 in FIG. 1A is to produce different phase steps that are defined as relative displacements in the direction perpendicular to grating lines between the source grating 104 and the phase-analyzer grating pair 122 which is composed of a phase grating 106 and an analyzer grating 108. Source grating system 120 is composed of several branches and at each branch, a source grating 104 is fixed. The source grating system 120 is designed in such a way that when each branch is aligned with the phase-analyzer grating pair 122, the relative displacement between the source grating 104 and the phase-analyzer grating pair 122 ranges from a small fraction of the period of the source grating 104 to one grating period phase-analyzer grating pair, the relative displacement between the source grating and the phase-analyzer grating pair ranges from a small fraction of the period of the source grating 104 to one grating period across different branches. In FIG. 1B, a motor-driven linear stage 116 moves the source grating 104 to produce different phase steps. The object O will be kept stationary while the gantry 112 will be rotating to take images during a scan. A computer 118 controls and synchronizes the operation of x-ray tube 102, detector 110, gantry 112 and gratings to perform the imaging process. The computer 118 also performs tomographic reconstruction and analyzes the data.

The DPC technique is able to produce one-dimensional or two-dimensional spatial coherence by applying an absorption grating (the source grating 104) to a high power x-ray tube 102 that has a focal spot size of hundreds of microns and a high x-ray output power (>10 kW). The line patterns 114 made of high atomic number materials of the source grating 104 can absorb almost all x-ray photons impinging on them while the grooves in between let all the x-ray photons pass through. The width of the grooves is designed to be comparable to the focal spot size of a micro-focus x-ray tube 102. Thus the source grating 104 divides a large focal spot x-ray tube 102 into several narrow line sources. Each of these line sources is able to produce sufficient spatial coherence at the direction perpendicular to the lines, while they are mutually incoherent. When proper parameters are chosen, these line sources contribute constructively in the imaging process. In a similar manner, the grating pattern can be designed as a matrix of multiple pinholes and each pinhole functions as a point source that is able to individually provide sufficient coherent length in both dimensions but mutually incoherent.

The phase-stepping algorithm [1] is used to calculate each DPC image, the physical principle of which is briefly explained as following: The phase grating 106 shows negligible absorption but substantial phase shift, dividing the x-ray beam into two first diffraction orders. The refracted beams then interfere and form periodical fringes at an integer or fractional Talbot distance where the analyzer grating 108 is placed. The period of the analyzer grating 108 is chosen to be the same as the period of the fringes. If the incident x-ray beam encounters an object before it reaches the phase grating 106, its wavefront will be perturbed by the object, leading to local displacement of the fringes. The phase stepping algorithm can be used to retrieve the encoded phase information based on detector images. An x-ray detector 110 with a pitch larger than the diffraction fringe period can be used to record the intensity images, which removes the restriction of an ultrahigh detector resolution that has a pitch even smaller than the diffraction fringes. In principle, while any of the three gratings (source grating 104, phase grating 106 and analyzer grating 108) is stepped, the detected intensity value of any pixel in the detector 110 is modulated by the position of the stepped grating. If the modulation function is transformed into Fourier domain, then the complex angle of the first Fourier component is the first derivative of phase at this pixel. The DPC image of an object acquired in this way is a raw DPC image. Usually the background phase distribution due to the non-uniformity of any of the grating systems 120 and 122 is acquired by the same process without an object in place, and the true DPC image of the object is acquired by subtracting the background phase distribution from the raw DPC image.

Figure 2:
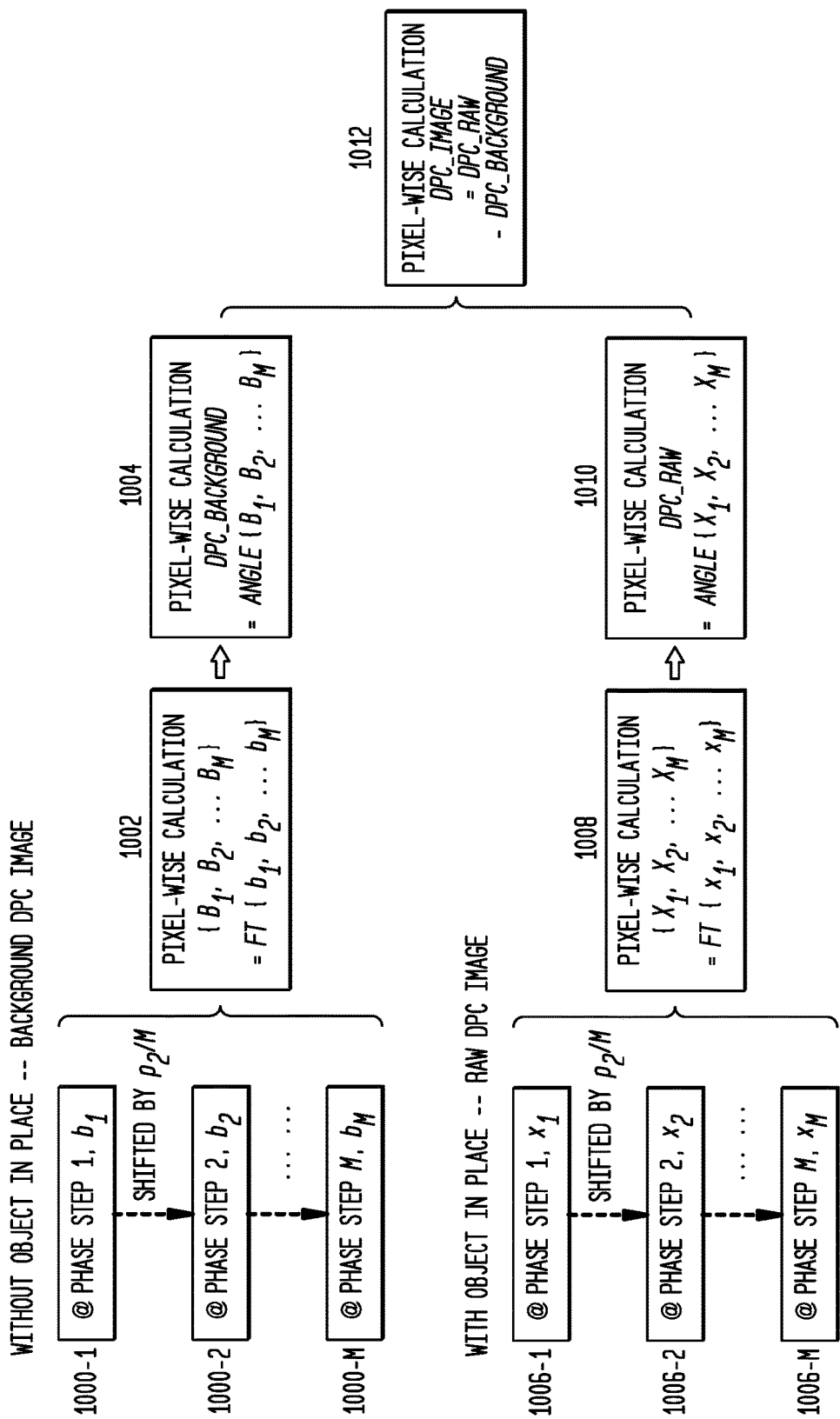
FIG. 2 demonstrates the phase-stepping algorithm.

The whole procedure is shown in FIG. 2. Without the object in place, in steps 1000-1 through 1000-M, background DPC images are taken at phase steps 1 through M. Pixel-wise calculations are performed in steps 1002 and 1004. With the object in place, in steps 1006-1 through 1006-M, raw DPC images are taken at phase steps 1 through M. Pixel-wise calculations are performed in steps 1008 and 1010. The final pixel-wise calculation in step 1012 calculates the final image from the DPC raw and background images.

It should be noted that the background information can be pre-stored for the background correction for a given DPC-CBCT system 100, and therefore it is not necessary to be acquired for every scan. Theoretically, at least two sampling points are needed to represent a periodic function if the period is known, and thus at least two phase steps are needed to perform the phase stepping algorithm. In practice, three or more sampling points are needed to avoid aliasing artifacts. As the source grating 104 usually has a much larger period than either the phase grating 106 or the analyzer grating 108, larger steps can be used for source grating stepping, which can greatly relax the requirement of mechanical precision. For example, the period of the source grating 104 can range from 30-200 µm, and thus for an eight-step scheme, each step is about 4-25 µm in length for source grating stepping. If either the phase grating 106 or the analyzer grating 108 is stepped using the eight-step scheme, each step should be less than 0.6 .mu.m because the period of the analyzer grating 108 is generally less than 5 µm. Similar mechanical requirement (of the order 4-25 µm) applies to both the rotation of the branch structure in FIG. 1(a) and the shifting of the linear stage 116 in FIG. 1(b). While each branch is aligned with the optical axis (FIG. 1(a)) or the source grating 104 is stepped once by a displacement of the linear stage 116 (FIG. 1(b)), an intensity image is acquired for this phase step, and these intensity images are then processed to calculate the DPC image using the method described above. In addition, an attenuation image can be obtained by summing up the phase stepping images to produce absorption contrast, and a darkfield image can be obtained by calculating ratio of the first Fourier component and the zeroth Fourier component to produce the contrast due to small-angle scattering caused by sub-micron structures.

The DPC images acquired from all view angles will be directly used for reconstruction instead of calculating the line integrals of phase coefficient first from the DPC images. Considering that the cone angle of the DPC-CBCT system 100 is small, the parallel beam approximation can be applied for tomographic reconstruction, and a filtered backprojection (FBP) algorithm with Hilbert filtering can be used [2]. The DPC images are row-wisely filtered using the Hilbert filter, and then are backprojected into the object space to calculate the 3-D distribution of the linear phase coefficient. When the object is fully covered by the x-ray beam at all view angles (no transverse truncation), the reconstruction result is accurate up to a constant. The reconstruction constant can be easily determined by setting the phase coefficient of surrounding air to zero. In the case of volume-of-interest (VOI) imaging where truncation occurs, this reconstruction method also works, but the image quality will be degraded by the background trend, and the reconstruction constant has to be determined using prior knowledge of the object. Besides, backprojection-filtration (BPF) algorithms can be modified for DPC-CBCT reconstruction because a differentiation operation is usually performed before backprojection while the DPC image is very similar to the intermediate result after the differentiation operation. This type of algorithm also has a good capability to handle severe truncations. The procedure of DPC-CBCT imaging using a typical BPF reconstruction comprises the same methods to obtain DPC images, and the only difference is the reconstruction method. The major steps are: (a) acquire raw intensity data from all view angles; (b) compute DPC images using the phases-stepping algorithm from the intensity data as shown in FIG. 2; (c) backproject the DPC images to the object space from all view angles; and (d) filter the backprojected data using desired filter(s) along specified direction(s). The projection images can be attenuation images, DPC images and dark-field images, and the reconstructed quantity are then respectively the attenuation coefficient, phase coefficient and density of sub-micron structures.

To further reduce image noise or reduce required dose while maintaining image quality which is clinically acceptable, an iterative reconstruction algorithms can also be used for DPC-CBCT reconstruction to compute the 3D phase coefficient, and the reconstruction becomes an solution of an optimization problem. One approach of the iterative reconstruction is to use the so-called compressed sensing method [4]. The idea of compressed sensing is that sparse information can be faithfully restored from severely undersampled signals by minimizing the L1 norm. Sparsity of a signal means that besides a small part of significant (non-zero) values, a large part of the signal is zero. In the case of DPC-CBCT imaging, although the reconstructed 3D image of phase coefficient is not sparse, it can be transformed into a sparse image by certain transforms. For example, as the 3D phase coefficient distribution is generally piecewisely constant, its gradient transform is sparse because significant values are concentrated only at feature edges. Therefore, the sparse transform can be a gradient transform and its L1 norm, which is usually referred as total variance (TV), can be iteratively minimized to let the reconstruction approach an optimal solution. Other transforms can be used in a similar manner as well if the transformed image is sparse. Compressed sensing can be incorporated into DPC-CBCT reconstruction either as a regularization term or as a constraint, and the general approach of solving an optimization problem can be applied to iteratively perform the computation.

Figure 3:
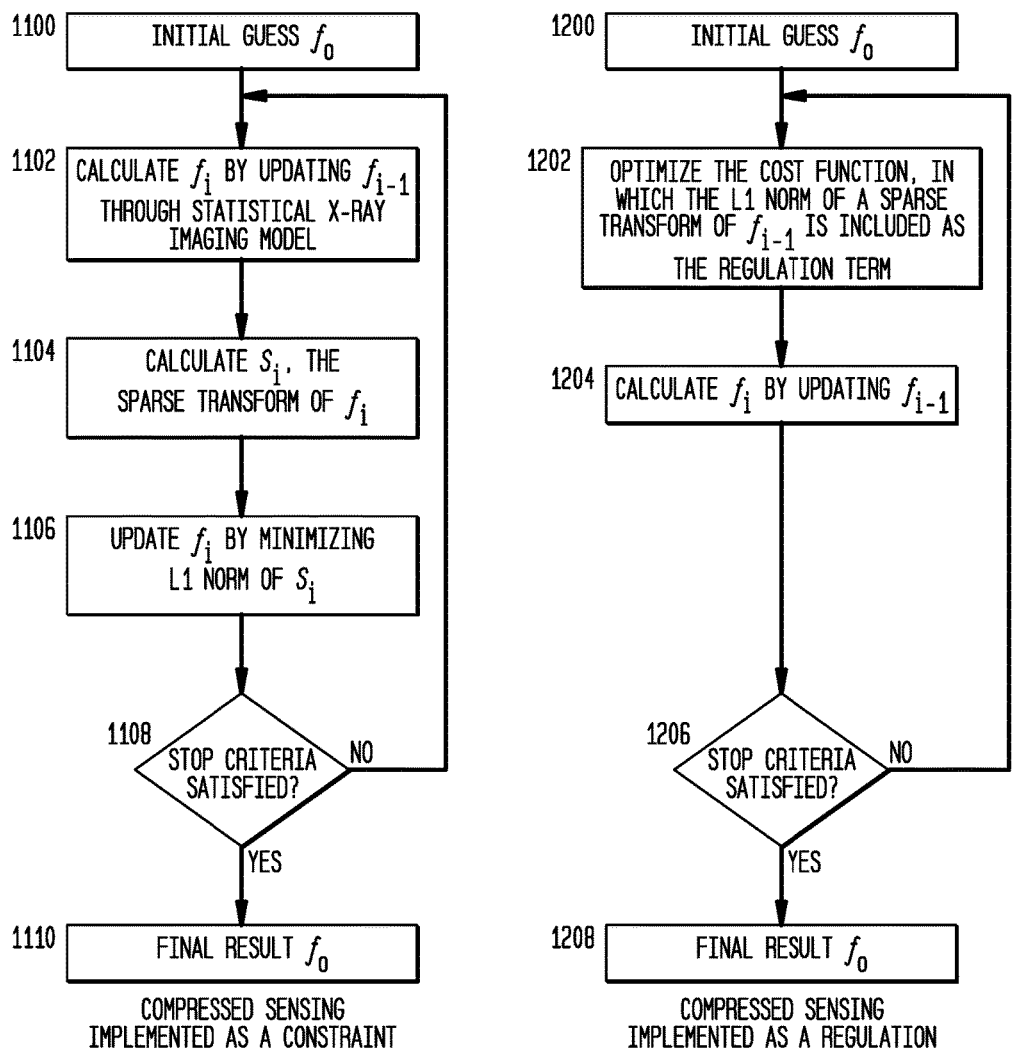
FIG. 3 demonstrates iterative reconstruction algorithm using compressed sensing method.

The flowchart of the compressed sensing-based iterative reconstruction algorithm is shown in FIG. 3. For compressed sensing implemented as a constraint, first, an initial guess $f_0$ is made in step 1100. In step 1102, $f_i$ is calculated by updating $f_{i-1}$ using a statistical x-ray imaging model. In step 1104, $S_i$, the sparse transform of $f_i$, is calculated. In step 1106, $f_i$ is updated by minimizing the L1 norm of $S_i$. In step 1108, it is determined whether the stop criteria are satisfied. If so, a final result $f_0$ is output in step 1110. Otherwise, the process returns to step 1102. For compressed sensing implemented as a regulation, first, an initial guess $f_0$ is made in step 1200. In step 1202, the cost function is optimized, in which the L1 norm of a sparse transform of $f_{i-1}$ is included as the regulation term. In step 1204, $f_i$ is calculated by updating $f_{i-1}$. In step 1206, it is determined whether the stop criteria are satisfied. If so, a final result $f_0$ is output in step 1208. Otherwise, the process returns to step 1202.

After properly modeling the optimization problem and making an initial guess, iterations are performed until the stop criteria is satisfied. The initial guess are repeatedly updated in each iteration before becoming the final solution.

Figure 4:
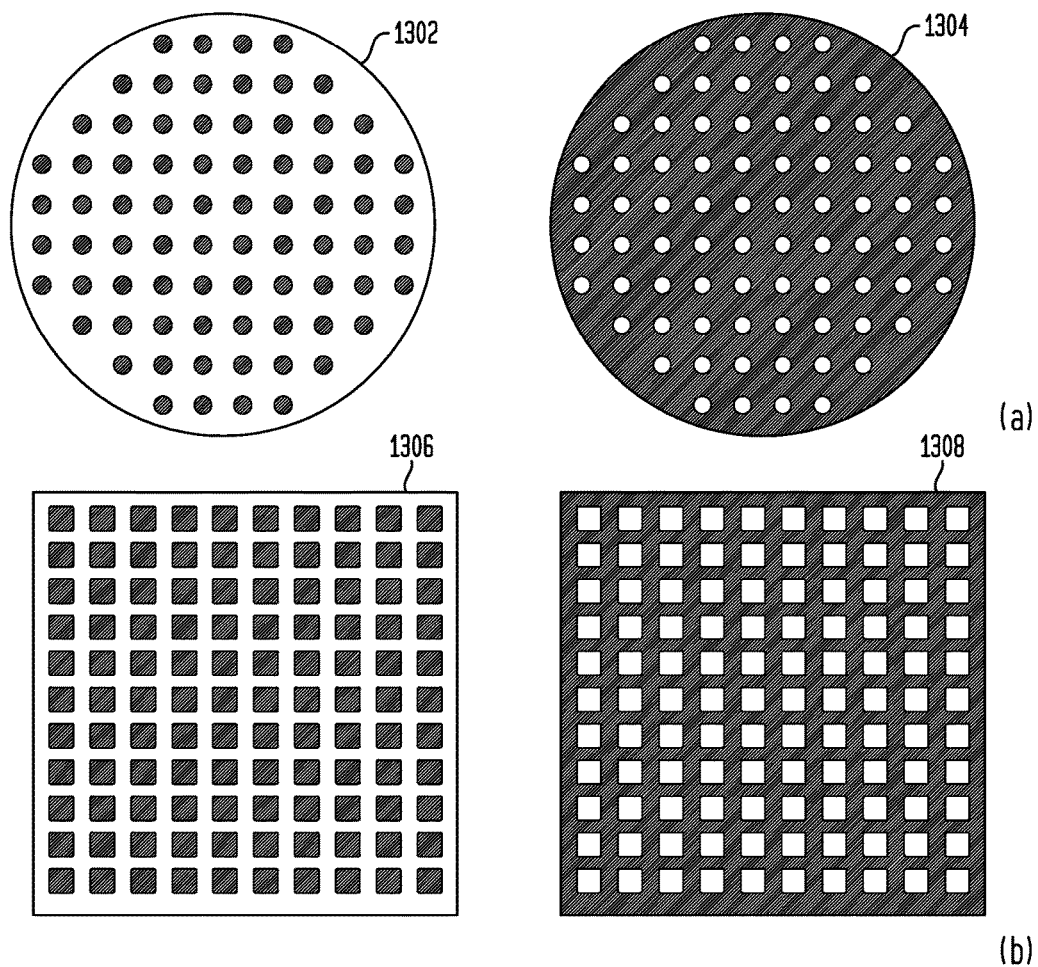
FIGS. 4A and 4B show designs of preferred two-dimensional grating embodiments.

In this disclosure the one-dimensional grating system with the corresponding scanning protocol and reconstruction algorithm is discussed in detail. It should be noted that it is straightforward to extend the one-dimensional grating system into a two-dimensional system where the source grating is composed of multiple point sources while the phase grating and the analyzer grating are composed of two-dimensional matrices. Some of the possible embodiments are shown in FIGS. 4A and 4B as 1302, 1304, 1306, and 1308. The phase-stepping algorithm should be performed in preferred directions (x, y, diagonal and etc) to extract the phase contrast equally in both x and y directions. A modification should be carried out for the cone beam reconstruction algorithm to deal with the phase gradient in both directions.

Major parameters of the proposed DPC-CBCT system 100 are listed in Table 1. A hospital-grade x-ray tube 102 is used for the DPC-CBCT system 100. The x-ray tube 102 has a focal spot size of 0.05 mm to 2 mm and an output power of several kilowatts to tens of kilowatts. It will operate at 10 kVp to 150 kVp. Generally it can be any kind of diagnostic imaging x-ray radiation sources, including mammography tubes, angiography tubes, CT tubes and other general purpose radiographic tubes, depending on the clinical applications.

TABLE 1

Major system parameters

| | |
|---|---|
| Focal spot size | 0.05 mm-2 mm |
| Peak voltage | 10 kVp-150 kVp |
| Detector pixel size | 10 μm-1000 μm |
| Detector frame rate | 0.5 fps-1000 fps |
| Detector dimensions | 3 cm × 3 cm-50 cm × 50 cm |
| Gantry rotation speed | >0.5 RPM |
| Detection Quantum Efficiency (DQE) of detector | >50% |
| Dynamic Range | >30,000:1 |
| The system spatial resolution | >2.5 lp/mm-25 lp/mm |

A two-dimensional detector 110 is used for the DPC-CBCT system 100. Unlike other phase-contrast imaging techniques, there is no strict requirement for an ultra high resolution detector, and the detector resolution can be ~10 μm-1000 μm, determined by the applications and expected image resolution. The frame rate of the detector 110 is 0.5 frames per second (fps) to 120 fps for different image acquisition protocols. For the potential application of breast imaging which requires high spatial resolution and high contrast resolution, the detector 110 should have a detection quantum efficiency (DQE) of >50%, dynamic range of >30,000:1. The system spatial resolution is expected to be over 2.5 lp/mm-25 lp/mm.

The source grating 104 is mounted as close to the focal spot as possible for the best field of view. It divides the x-ray beam into many line sources, and the width of each line source is generally less than 50 μm to provide sufficient spatial coherence. The phase grating 106 is mounted right behind the object and yields a phase difference of PI between grooves and ridges. The period of the phase grating 106 is 2 μm to 8 μm. The analyzer grating 108 is mounted right at the surface of the detector 110 and it attenuates x-rays to 20% to 80% at grooves by strongly attenuation materials. The period of the analyzer grating 108 is the same or half of that of the phase grating 106 (up to a magnification factor which is close to 1.0), depending on the distance between the two gratings, which can be fractional Talbot distances or integer Talbot distances. The distance between the source grating 104 and the phase grating 106 and the distance between the phase grating 106 and the analyzer grating 108 determine the period of the source grating 104, which is usually 30 μm to 200 μm. The sizes of gratings are designed to cover the field of view for the specific applications of the DPC-CBCT system 100. Major grating parameters are listed in Table 2. A possible variation would use two-dimensional phase contrast gratings. It should be noted that such a grating design is ideal for parallel x-ray beam or an x-ray beam with small cone angle as the grating grooves are parallel. When a larger cone angle (>5 deg) is used, it would be better to use focused gratings that is designed and fabricated with consideration of the diverging x-ray beam.

TABLE 2

Major grating parameters

| | Source grating 104 | Phase grating 106 | Analyzer grating 108 |
|---|---|---|---|
| Grating pitch p (μm) | 30-200 | 2-8 | Same or half that for phase grating 106 |
| Groove height t (μm) | 40-200 | 10-50 (phase shift of PI) | 10-100 |
| Duty cycle | Line width <50 μm | 50% | 50% |

Figure 5:
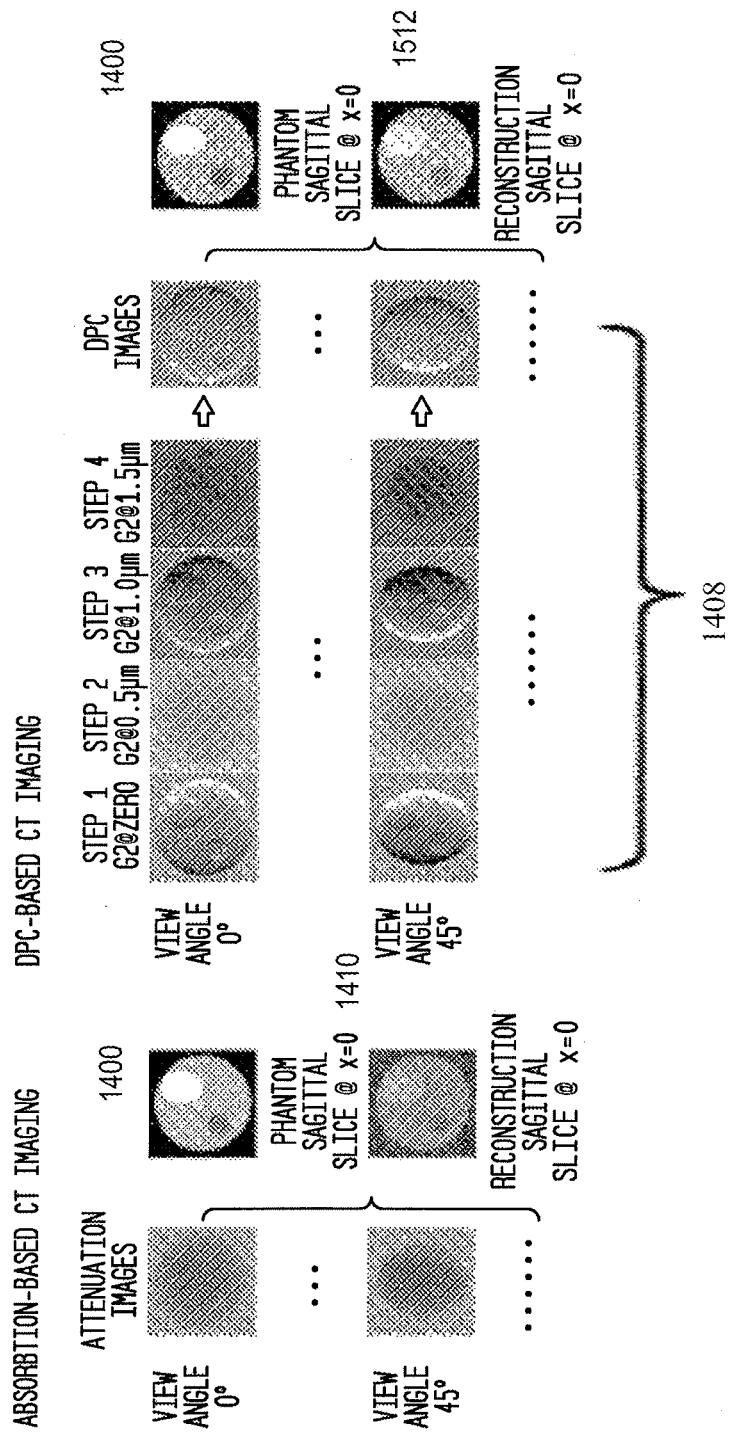
FIGS. 5A and 5B compare the imaging process of a DPC-CBCT and a conventional absorption-based CBCT.

The x-ray tube 102, detector 110 and grating system are mounted on a rotation gantry 112 that can achieve a speed of 0.5 revolutions per minute (RPM) to 60 RPM or larger. The patient is kept stationary during a scan. FIGS. 5A and 5B compare computer simulation images of a simple numerical phantom 1400 using the attenuation technique and the DPC technique with the same total exposure level and reconstructed spatial resolution. The numerical phantom 1400 is composed of three ellipsoids and is placed at the center of the scanning plane. The attenuation-based CBCT takes one intensity image 1408 at each view angle, and a sagittal slice 1410 is reconstructed, as demonstrated in FIG. 5A. The DPC-based CBCT, as illustrated in FIG. 5B, takes four intensity images at each view angle with the analyzer grating 108 shifted by four different steps, and the exposure to each intensity image is a quarter of that of the attenuation-based image. The four intensity images are then processed to retrieve the DPC image using the principle of the phase-stepping algorithm. The same sagittal slice is then reconstructed as 1512 from the set of DPC images. The phantom image of the same sagittal slice is shown for comparison. It can be observed that both DPC projection and reconstruction images show much higher CNRs than that of the absorption projection and reconstruction images. As expected, the measured contrast in the DPC-CBCT reconstruction image is about 1000 times higher than that of attenuation-based reconstruction, while the noise level of DPC-CBCT is 40 times higher than that of attenuation-based reconstruction. Then measured CNR is 28.2 in the DPC-CBCT reconstruction and 0.81 in the attenuation-based reconstruction, resulting in a CNR improvement of about 35 times. Thus with the same dose level and spatial resolution, DPC-CBCT imaging possibly provides an order of magnitude improvement CNR over that by attenuation-based CBCT. We have performed additional simulation to prove that with 25 lp/mm (20 μm) resolution and mammographic dose level, DPC-CBCT can achieve clinically acceptable CNR.

In the proposed DPC-CBCT technique, the data acquisition geometry is not limited to the circle orbit. The gantry 112 can be controlled and moved by at least one motor to perform scans along various orbits, including a spiral geometry, a circle-plus-line geometry and a circle-plus-arc geometry.

Figure 6:
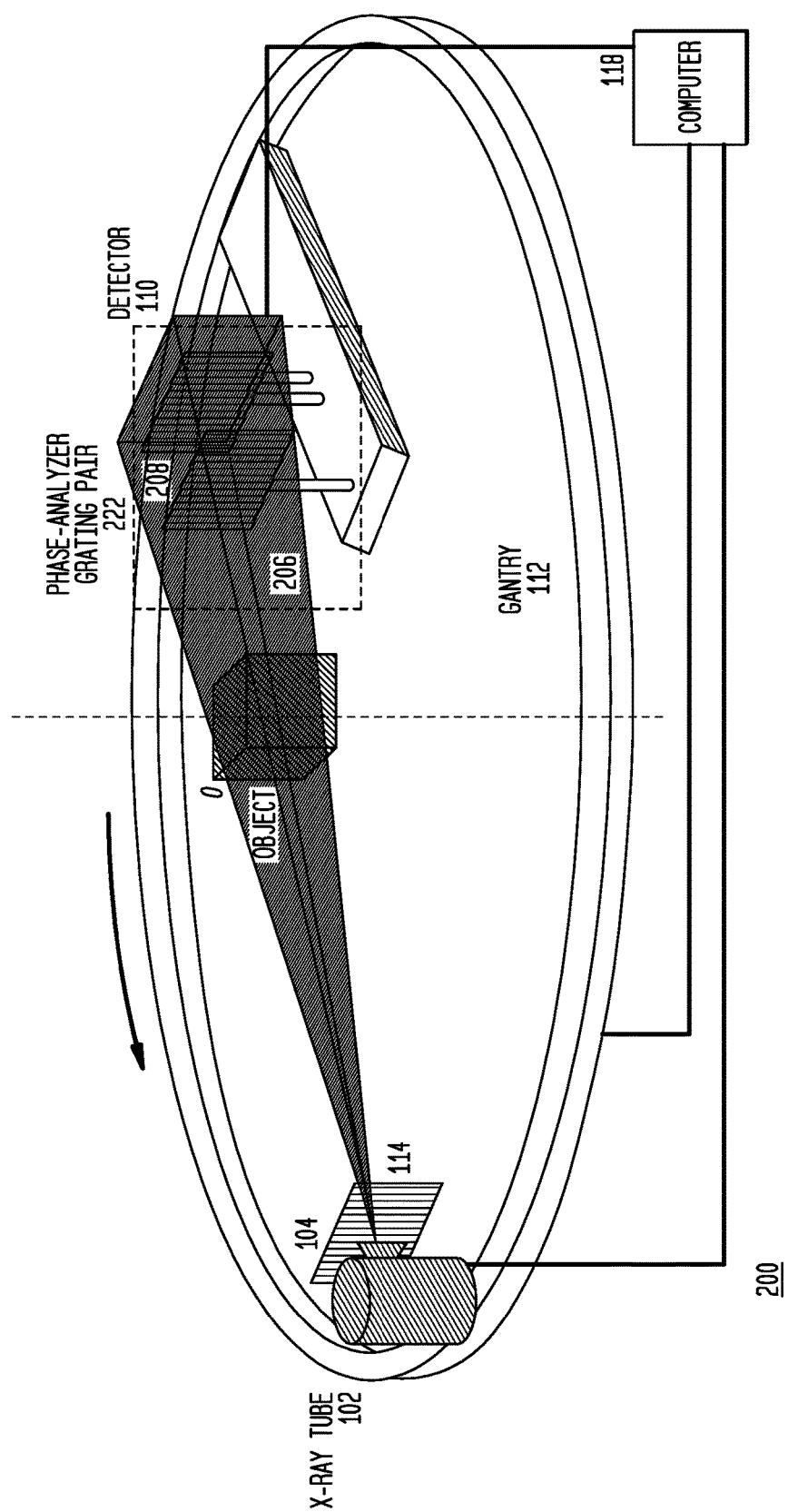
FIG. 6 is a schematic diagram showing a system according to a second preferred embodiment.
Figure 7:
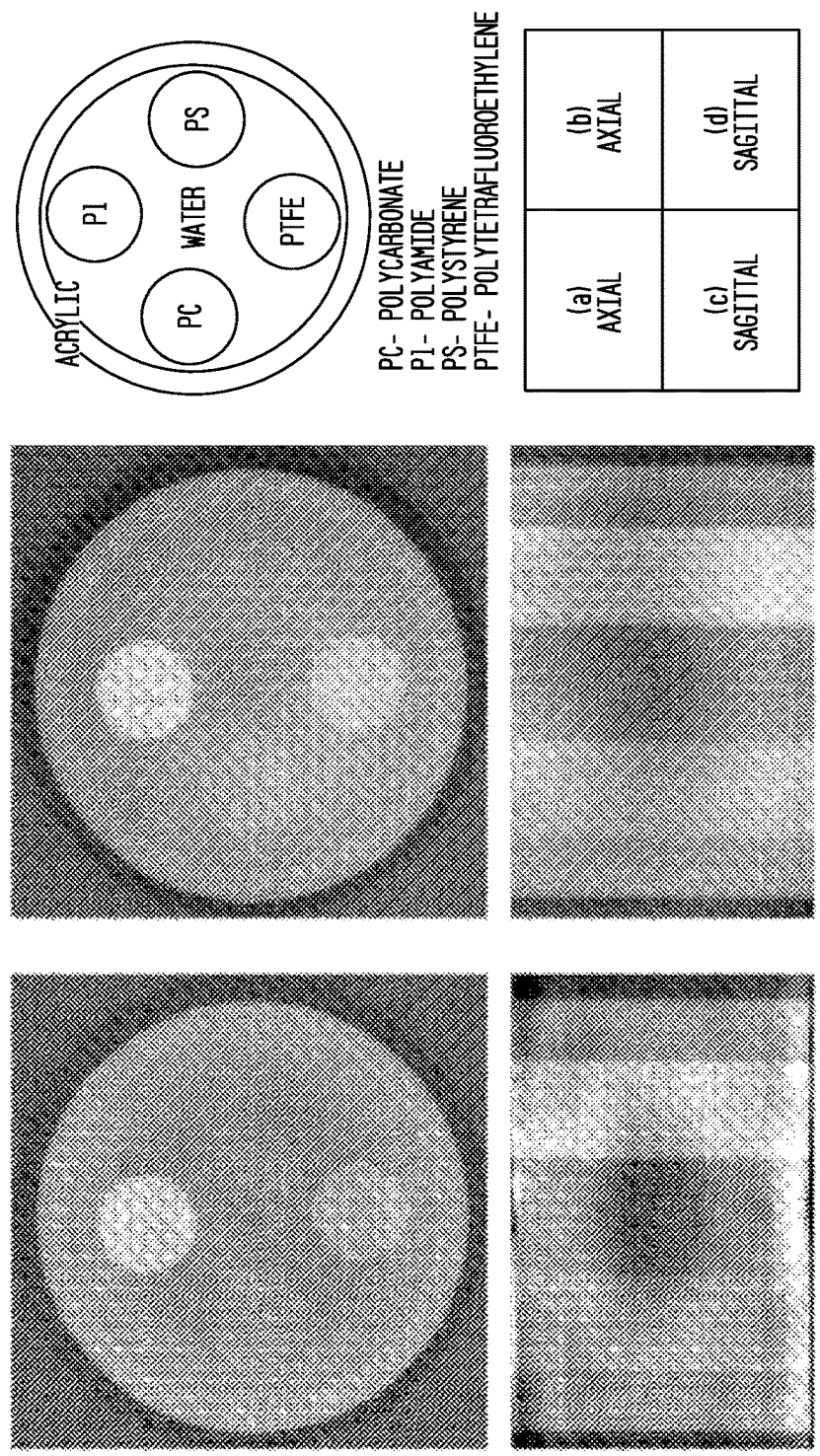
FIG. 7 compares the reconstruction images from the phase-stepping approach and the moiré pattern-based approach

The second preferred embodiment is a variation of the first preferred embodiment. The major advantage of the second preferred embodiment is that all the information can be obtained through a single moire pattern image and no stepping is required [3]. This reduces the complexity of image formation and makes fast imaging possible. As shown in FIG. 6, the second preferred embodiment has the same system components as that of the first preferred embodiment in FIG. 1B except that the linear stage is removed. In the DPC-CBCT system 200, in the phase-analyzer grating pair 222, the phase grating 206 and analyzer grating 208 are slightly misaligned to produce the moire pattern, which is distorted with the presence of an object in the x-ray beam as a result of phase change. By analyzing the moire pattern using a Fourier transform approach, it is possible to retrieve the attenuation image from the zeroth Fourier component, the differential phase contrast (DPC) image from the first Fourier component and the dark field image from the ratio of the previous two. The reconstruction algorithms described before, either FBP-type or iterative-type, can be directly applied to reconstruct the 3D phase coefficient using the retrieved DPC images. FIG. 7 compares phantom study results using the phase stepping approach and the moire pattern-based approach.

It should be noted that the analyzer grating 208 does not have to be an attenuation grating as that for the first embodiment. Instead, it could be a second phase grating that produces significant phase change but negligible amplitude change. A phase-phase grating pair will also produce similar moiré patterns if the detector is placed at an appropriate location, which could be a fractional Talbot distance or an integer Talbot distance.

The present invention allows the implementation of a DPC-CBCT system to detect and characterize breast tumors and microcalcifications with a spatial resolution up to 25 lp/mm, which is comparable to that of pathology images and results in the significant reduction of biopsy rate. The following design considerations are involved. The first design consideration is to design and construct a coherent x-ray radiation source that combines the hospital-grade x-ray tube 102 with a specially designed and constructed source grating (104) to provide a stable coherent radiation source with 5 cm field of view (FOV) coverage or larger. The second design consideration is to fabricate high quality gratings with uniform microstructures to cover the proposed FOV. The third design consideration is to design and construct an appropriate 2D detector system which has ultra-high spatial resolution (up to 20 μm for detector pitch), a high detective quantum efficiency (DQE), high dynamic range, minimal geometric distortion and excellent linearity. The fourth design consideration is to develop a practical DPC-CBCT data acquisition scheme along with accurate and efficient phase stepping algorithms and DPC-CBCT reconstruction algorithms. The fifth design consideration is to design and construct the proposed HBCT (hybrid breast CT) system (CBBCT plus DPC-CBCT) to ensure a targeting DPC-CBCT scan and proper coverage of the volume of interest.

As discussed above, the requirement for a phase contrast imaging system is that the incident x-ray beam should be spatially coherent to a certain degree, and it is possible to perform DPC-CBCT imaging using high power hospital-grade x-ray tubes with an attenuation grating. To meet this challenge, we propose to select a high-power mammography tube or general radiography tube with an anode power larger than 10 kW and couple it with a specially designed source grating 104 in FIG. 1, where the x-ray tube 102 can be considered as being divided into many narrow line sources with width of 10~50 μm, and these line sources are individually spatially coherent in the direction perpendicular to grating grooves but mutually incoherent. With this design, the x-ray tube 102 is able to provide sufficient x-ray flux even with the strong attenuation of the source grating 104. The high aspect ratio (the ratio between groove height and groove width) of the source grating 104 may affect the field of view, and it is important to mount the source grating 104 as close to the focal spot as possible (preferably <1 cm) for larger FOV.

The gratings used for DPC-CBCT imaging will be fabricated using Micro-Electro-Mechanical Systems (MEMS) nanofabrication facilities, including photolithography, physical etching, chemical etching, deposition and electroplating. The major challenge is the high aspect ratio of the gratings (the ratio between groove height and width), which makes etching and electroplating difficult. For the phase grating and the analyzer grating, the aspect ratio can be as high as 15 to 40, which causes difficulties in etching with straight edges or growing gold into deep grooves. To solve this issue, a high-quality <110> orientated single crystal silicon substrate (Nova Electronic Materials, Flower Mound, Tex.) will be used that is highly selective in a preferred direction, with which it is easier to form sharp and deep edges by wet etching using potassium hydroxide (KOH). A nitride layer will be used as the mask and the atomic layer deposition (ALD) will be used to epitaxially grow the seed layer of gold. Next, electroplating will be used to grow the gold layer on top of the seed layer following its own crystal structure. Other elements with high atomic number like Pt, Hf or Ta can be used as well. Currently the standard large scale MEMS technique is limited to silicon wafers with a diameter of 4 inch, but it is expected to achieve much large silicon wafer size and also grating size in the future. In addition, wafers with small thickness will be used to reduce the unnecessary x-ray attenuation of any grating and to reduce the x-ray exposure to patients, Most of the currently available detectors for hard x-rays, including thin film transistor flat panel detector (TFT-FPD) (for example, PaxScan 4030CB by Varian Medical Systems, Salt Lake City, Utah), charge-coupled device (CCD) detector (for example, Alta F16M by Apogee Imaging Systems, Roseville, Calif.), complementary metal-oxide-semiconductor (CMOS) detector (for example, Shad-o-Box 4K by Teledyne Rad-icon Imaging Corp., Sunnyvale, Calif.), and photon-counting detector (for example, Medipix3 by the European Organization for Nuclear Research, Meyrin, Switzerland) can be used. Appropriate scintillators should be chosen for the best x-ray energy response. However, for the purpose of breast imaging, which concerns the small size of microcalcifications (as small as 0.2 mm) and low contrast resolution among soft tissues, some special requirements should be specified. The detector should have a dynamic range of >30,000:1 (or >16 bit A/D conversion), a detective quantum efficiency (DQE) of >50% and a spatial resolution of the system should be 2 lp/mm-25 lp/mm. A higher frame rate of 0.5 fps-1000 fps is expected that makes it possible for faster scanning process and reduced motion artifacts.

Figure 8:
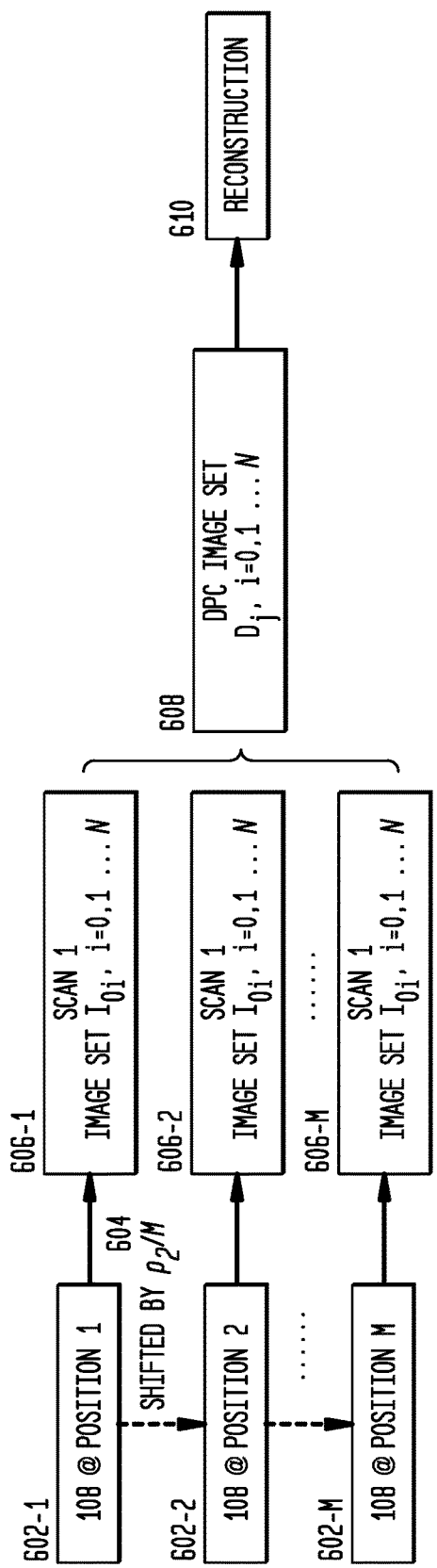
FIG. 8 is a flow chart showing a scanning protocol.

The conventional CBCT scanning protocol is quite straightforward, as only one x-ray exposure is needed to acquire an absorption image at each view angle. The second preferred embodiment can perform in the same way as a conventional CBCT scan as no stepping is needed. The first embodiment, however, requires at least three x-ray exposures at any view angle, and the source grating 104 will be shifted to different position for each exposure to acquire the phase-stepping images, which will then be processed to compute the final images (attenuation, DPC, or dark-field) at this view angle. Thus the phase-stepping algorithm for phase retrieval adds more complexity in the DPC-CBCT scanning protocols. We propose to divide a complete DPC-CBCT scan into several sub-scans, the source grating system 120 being rotated to the next branch (FIG. 1A) or the source grating 104 being shifted by the linear stage 116 (FIG. 1B) before each sub-scan but fixed during each sub-scan. This will remove the positioning error due to repeated forward-backward movement of the source grating 104. Then the phase-stepping algorithm will be performed to calculate the DPC images at each view angle, and the reconstruction algorithm will be performed to calculate the tomographic images. Assuming that M phase-stepping images (M≥3) are needed to calculate the DPC image at each view angle and N DPC images are needed for tomographic reconstruction, the whole scanning process is illustrated in FIG. 8. The source grating 104 is positioned in a plurality of steps 602-1, 602-2, . . . , 602-M in a plurality of positions; between those steps, it is repositioned in step 604. When the source grating 104 is in each of the positions, a scanning step 606-1, 606-2, . . . , 606-M is performed to take an image set. The scans result in a DPC image set in step 608, which is reconstructed in step 610. Either the FBP-type or iterative-type reconstruction algorithms can be used for reconstruction, and the compressed sensing-based iterative algorithm (as described in a previous paragraph and FIG. 3) can be applied to further reduce image noise or reduce required dose while maintaining image quality which is clinically acceptable. Phase wrapping due to large phase derivatives or high noise level in intensity images is the major problem that may cause false phase information in DPC images, appearing as discontinuities. This problem will be solved by detecting singularities based on wavelet analysis and correcting singularities by interpolation.

High precision, good stability and accurate alignment are required in construction and calibration of the DPC-CBCT system 100 and 200, which concern mostly the position of the source gratings 104, which should be mechanically stable down to a scale of approximately one-tenth of its grating period (approximately 3-20 μm). The similar scale of stability also applies to the precision of each step, which can be a rotation or a transverse motion. Another concern is that the relative position of the phase grating 106 and 206 and the analyzer grating 108 and 208 should be stabilized. The grating mounts will be equipped with precise one-way translation and three-way rotation to make the gratings 106 and 108 well aligned with their grooves parallel to each other, or to make the gratings 206 and 208 misaligned by a desired small angle. The angular sensitivity of grating mounts is expected to be within a couple milliradians to minimize a possible moire pattern for DPC-CBCT system 100 or to generate a desired moire pattern for DPC-CBCT system 200. As the gantry 112 will be rotated during a scan, it is a mechanical challenge to stably rotate the source-detector set while keeping the relative position between the x-ray tube 102, the detector 110 and the source grating system 120 unchanged with an accuracy of a few microns.

Large-scale fabrication techniques with silicon wafers are under development that are able to make gratings as large as 30 cm×30 cm. The advance of MEMS techniques may also make it possible to make two dimensional gratings that are able to show phase contrast equally well in both directions and eliminate the possible problems with object orientation. There are no major technical obstacles in fabrication of large-area (up to 50 cm×50 cm), high-resolution (>25 lp/mm) detectors using CMOS or CCD techniques, and the frame rate is expected to be improved by tens of times with novel parallel acquisition and fast caching techniques. Hence the field of view will be greatly enlarged for ultrahigh resolution breast imaging or whole body imaging. Though the x-ray tube 102 is not a limitation for DPC imaging, emerging techniques of compact micro-focus x-ray tubes, including laser plasma tubes and liquid metal target tubes will further improve image resolution and simplify the system design by removing the grating 104 that may increase field of view and improve exposure uniformity.

With the technique advances described above, the DPC-CBCT system is expected to scan faster (achieve a few seconds/scan), cover larger objects, and provide higher spatial resolution, which makes it possible to use the DPC-CBCT imaging as both screening and diagnosis tools. The screening DPC-CBCT system will be designed with a lower spatial resolution (~100-75 μm) and the patient will be exposed with very low exposure (lower than that of two view screening mammography). The diagnostic DPC-CBCT system will be designed with a higher spatial resolution (~50-20 μm) and the patient dose will be equivalent to that of a diagnostic mammography (~6 mGy for average size normal density breast). Currently the VOI breast imaging is designed as a hybrid system with two sub-systems: a CBCT system and a DPC-CBCT system. In the future it can be further simplified as a single DPC-CBCT imaging system that can perform both a screening scan and a diagnostic VOI scan by switching the field of view, different resolutions (standard resolution for large field view and screening imaging and ultrahigh resolution for small field and diagnostic imaging) and different readout rates (0.5 frame/s-120 frame/second).

Figure 9A:
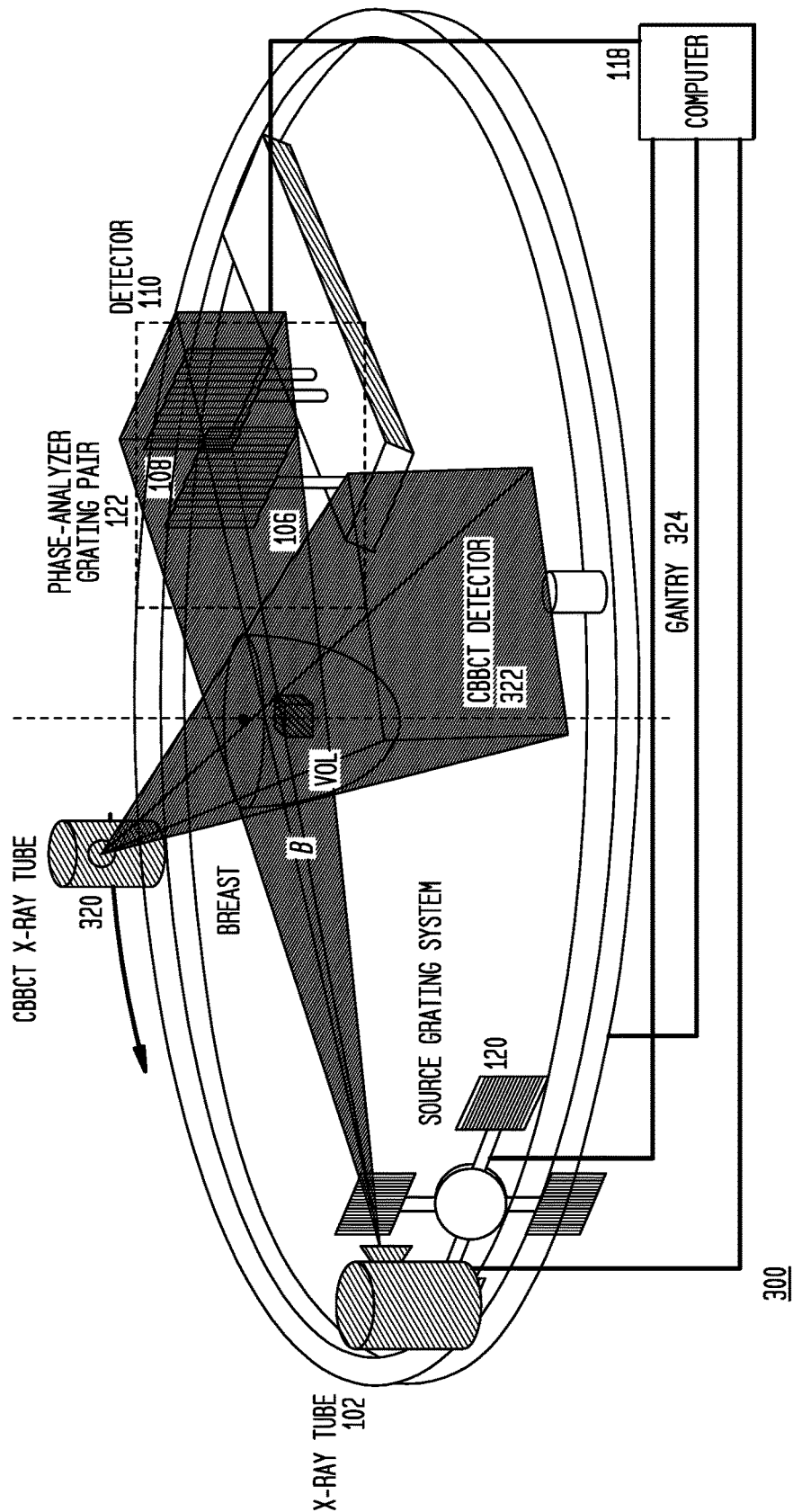
FIGS. 9A and 9B are schematic diagrams showing a system according to a third preferred embodiment.
Figure 9B:
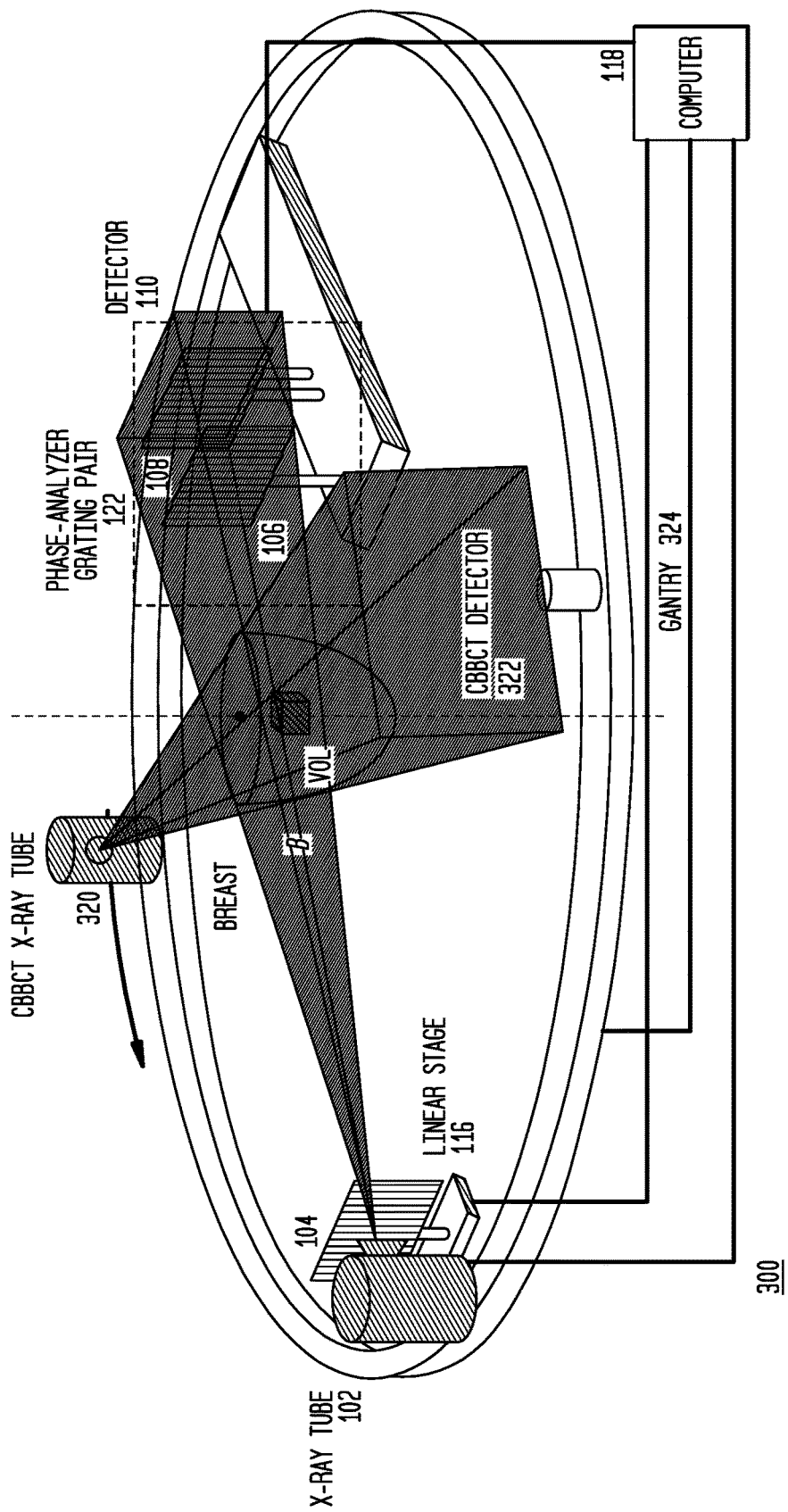

Our first application of the proposed DPC-CBCT technique is a cone beam breast CT modality for breast cancer diagnosis to reduce the biopsy rate, while this technology can be also used for whole body imaging as well as angiography and bone imaging. A third preferred embodiment combines current cone beam CT with DPC-cone-beam CT to form a hybrid cone beam CT that is capable of acquiring both 3D high resolution cone beam CT imaging and ultrahigh resolution DPC-cone-beam CT imaging. FIGS. 9A and 9B show one possible design for a hybrid cone-beam CT system 300 for breast imaging. The hybrid cone-beam CT system 300 includes a current cone beam breast CT (CBBCT) system, which is mainly composed of an x-ray tube 320 and a flat-panel detector 322. On the same rotary gantry 324, a DPC-CBCT system 100 (as the first preferred embodiment) is constructed which is mainly composed of an x-ray tube 102, a high-resolution detector 110, a phase-analyzer grating pair 122 and a source grating system 120 as shown in FIG. 9(A). Or the source grating system 120 can be replaced by a source grating 104 and a linear stage 116 as shown in FIG. 9(B). The CBBCT system is used to scan the whole breast B first and find out the 3D location of any suspicious volume; the breast is then translated and positioned such that the suspicious volume is centered in the field of view (FOV) of the DPC-CBCT system 100; finally the DPC-CBCT system 100 performs an ultrahigh-resolution scan of a volume of interest (VOI), and the phase coefficient of the 3D volume is reconstructed. This ultrahigh-resolution DPC-CBCT scan is expected to reveal ducts (<0.25 mm in width), small vessels (<0.5 mm in width) and microcalcifications (<0.2 mm in diameter) for diagnosis and treatment of breast cancers.

Figure 10:
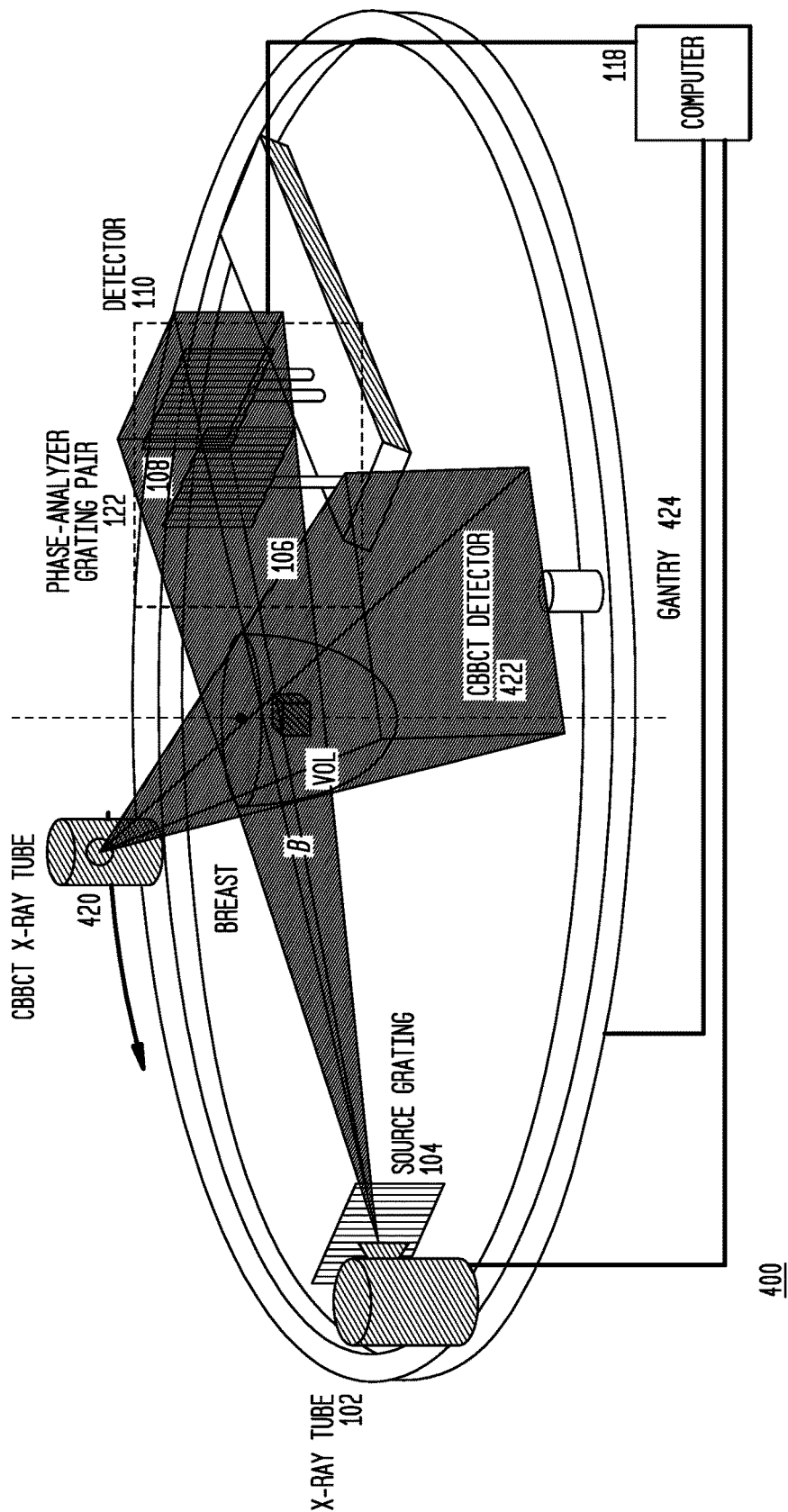
FIG. 10 is a schematic diagram showing a system according to a fourth preferred embodiment.

The fourth preferred embodiment is a variation of the hybrid system as shown in FIG. 10, which is actually a combination of the moire pattern-based system (second preferred embodiment) and the current CBBCT system comprising x-ray tube 420 and detector 422 on gantry 424. It should be noted that as no stepping is required in the hybrid cone-beam CT system 400, it can perform fast data acquisition, which makes dynamic imaging possible using this system.

It should be noted that all the four embodiments can be performed in a spiral scan mode to increase the coverage by moving the object along the rotation axis while the gantry is rotating. There are no theoretical or mechanical difficulties for this application extension.

To emphasize the main idea of this invention, the keys to successful implementations of all the four embodiments concerns mechanical robustness and patient dose. Two solutions have been addressed in this invention to obtain a robust design for a practical rotating-gantry system. The first is that in all the four embodiments, the relative position of the phase grating and the analyzer grating is always fixed, and they are referred to as a single unit called phase-analyzer grating pair. The imaging performance is very sensitive to the relative position of the phase grating and the analyzer grating, and a small displacement of the order of 0.1 μm will introduce errors and artifacts. Therefore it is not practical to step either of the two gratings in a rotating-gantry system because such a small error is unavoidable in mechanical stepping. In our invention, however, such an error is eliminated by using fixed phase-analyzer grating pair, and because the source grating has a much large period than the analyzer grating, the tolerance of mechanical error is greatly improved. The second solution is that the concept of phase stepping is implemented using a dial source grating system composed of branches, which is more robust that a linear stage for a rotating-gantry system.

There are also two solutions proposed to reduce patient dose in this invention. In the setup of a grating-based DPC-CBCT system, the phase grating and the analyzer grating are positioned between the patient and the detector. Because of this phase-analyzer grating pair, the x-rays passing through the patient are further attenuated by over 50% before reaching the detector. The attenuation after passing through the patient is very unfavorable in dose efficiency because the x-ray dose is not fully utilized to generate detector images. Two solutions are proposed in this invention. The first is to reduce the thickness of silicon wafers to reduce attenuation, which applies for all the four embodiments. Given that the standard silicon wafer has a thickness of 0.5 mm while the height of the grating structure is less than 50 μm (0.05 mm), the wafer thickness can be further reduced without impairing the grating structure. Surely to provide sufficient mechanical strength, the wafer thickness should not be too small. Experiment shows that one piece of 0.5 mm-thick silicon wafer attenuates 30% of x-rays at 40 kVp. If the wafer thickness is reduced to 0.25 mm, it will attenuate only 16% of x-rays, The second is to replace the analyzer grating with another phase grating, which applies for the second and the fourth embodiments. Besides the attenuation by the silicon wafer, an analyzer grating attenuates additional ~50% of x-rays. because of its gold structures. If the analyzer grating is replaced by another phase grating, the addition attenuation of 50% can be eliminated. The x-rays reaching the detector can be doubled for a phase-phase grating pair compared to a phase-analyzer grating pair.

While preferred embodiments and variations thereon have been disclosed above, those skilled in the art who have reviewed the present disclosure will readily appreciate that other embodiments can be realized within the scope of the invention. For example, numerical values are illustrative rather than limiting. Also, any suitable technique or materials for manufacturing the grating can be used. Furthermore, the utility of the present invention is not limited to breast imaging, but instead can be applied to any biological or non-biological imaging. Therefore, the present invention should be construed as limited only by the appended claims.

We claim:

1. A method for imaging an object, the method comprising:
    (a) acquiring a plurality of background images related to non-uniformity of a grating system from all view angles by an imaging process without the object in place wherein the grating system comprises a steppable source grating that steps in a direction transverse to a plane to which the source grating confirms;
    (b) acquiring a plurality of raw projection images from all view angles of the object by differential phase contrast (DPC) imaging process that uses an x-ray source, a detector, and the grating system to acquire a plurality of intensity images from which the plurality of raw projection images are derived, said plurality of intensity images being acquired by stepping the steppable source grating for each of the plurality of raw projection images;
    (c) acquiring a plurality of corrected projection images from all view angles of the object comprising calculating each corrected projection image by removing a background image of the plurality of background images from a raw projection image of the plurality of raw projection images at each of the view angles;
    (d) performing three-dimensional (3D) computed tomography reconstruction of the object using the plurality of corrected projection images from all view angles; and
    (e) displaying images of the object derived from the three-dimensional (3D) computed tomography reconstruction.

2. The method of claim 1, wherein the object is a human breast.

3. The method of claim 1, wherein the three-dimensional (3D) computed tomography reconstruction is cone-beam computed tomography reconstruction.

4. The method of claim 1, wherein the plurality of raw projection images are DPC images and the three-dimensional (3D) computed tomography reconstruction is a matrix of 3D distribution of phase coefficient.

5. The method of claim 1, wherein the plurality of raw projection images are attenuation images and the three-dimensional (3D) computed tomography reconstruction is a matrix of 3D distribution of attenuation coefficient.

6. The method of claim 1, wherein the plurality of raw projection images are dark-field images and the three-dimensional (3D) computed tomography reconstruction is a matrix of 3D distribution of the density of sub-micron structures.

7. The method of claim 1, wherein the grating system further comprises a phase grating and an analyzer grating.

8. The method of claim 1, further comprising stepping the steppable source grating a plurality of times within one period and acquiring an intensity image at each step.

9. The method of claim 8, wherein a differential phase contrast image is computed from the plurality of intensity images.

10. The method of claim 8, wherein an attenuation image is computed from the plurality of intensity images.

11. The method of claim 8, wherein a dark-field image is computed from the plurality of intensity images.

12. The method of claim 1, wherein acquiring a plurality of background images comprises measuring a background image once and pre-storing the background image to correct the plurality of raw projection images from all view angles.

13. The method of claim 1, further comprising, before step (b):

(i) imaging the object with a second imaging process different from the imaging process of step (a)-(e) to determine a region of interest in the object; and (ii) positioning the object so that the region of interest is positioned for steps (b)-(e).

14. The method of claim 13, wherein the second imaging process is computed tomography.

15. The method of claim 14, wherein the computed tomography is cone-beam computed tomography.

16. The method of claim 1, wherein step (b) comprises moving the x-ray source and the detector relative to the object to define a data acquisition geometry.

17. A system for imaging an object, the system comprising:
an x-ray source;
a detector;
a grating system comprising a steppable source grating that steps along an axis from the x-ray source to the detector;
a gantry configured to support the x-ray source, the detector, and the grating system relative to the object; and
a computer configured to control at least the x-ray source, the grating system and the detector to carry out the following operations:
(a) acquiring a plurality of background images related to non-uniformity of the grating system from all view angles by an imaging process without the object in place;
(b) acquiring a plurality of raw projection images from all view angles of the object by differential phase contrast (DPC) imaging process that uses the x-ray source, the detector, and the grating system to acquire a plurality of intensity images from which the plurality of raw projection images are derived, said plurality of intensity images being acquired by stepping the steppable source grating for each of the plurality of raw projection images;
(c) acquiring a plurality of corrected projection images from all view angles of the object comprising calculating each corrected image by removing a background image of the plurality of background images from a raw projection image of the plurality of raw projection images at each view for all view angles;
(d) performing a three-dimensional (3D) computed tomography reconstruction of the object using the plurality of corrected projection images from all view angles; and
a display facility configured to display images of the object derived from the three-dimensional (3D) computed tomography reconstruction.

18. The system of claim 17, wherein the three-dimensional (3D) computed tomography reconstruction is cone-beam three-dimensional (3D) computed tomography reconstruction.

19. The system of claim 17, wherein the plurality of raw projection images are DPC images and the three-dimensional (3D) computed tomography reconstruction is a matrix of 3D distribution of phase coefficient.

20. The system of claim 17, wherein the plurality of raw projection images are attenuation images and the three-dimensional (3D) computed tomography reconstruction is a matrix of 3D distribution of attenuation coefficient.

21. The system of claim 17, wherein the plurality of raw projection images are dark-field images and the three-dimensional (3D) computed tomography reconstruction is a matrix of 3D distribution of the density of sub-micron structures.

22. The system of claim 17, wherein the grating system further comprises a phase grating and an analyzer grating.

23. The system of claim 17, wherein the computer is further configured to carry out the following operation: stepping the steppable source grating a plurality of times within one period and acquiring an intensity image at each step.

24. The system of claim 23, wherein the computer is further configured to carry out the following operation: computing a differential phase contrast image from the plurality of intensity images.

25. The system of claim 23, wherein the computer is further configured to carry out the following operation: computing an attenuation image from the plurality of intensity images.

26. The system of claim 23, wherein the computer is further configured to carry out the following operation: computing a dark-field image from the plurality of intensity images.

27. The system of claim 17, wherein the computer is further configured to carry out the following operation: measuring a background image once and pre-storing the background image pre-stored to correct the plurality of raw projection images from all view angles.

28. A system for imaging an object, the system comprising:
an x-ray source;
a detector;
a grating system comprising a source grating, a phase grating, and an analyzer grating, wherein the phase grating and the analyzer grating are misaligned to produce a moire pattern;
a gantry configured to support the x-ray source, the detector, and the grating system relative to the object; and
a computer configured to control at least the x-ray source, the grating system and the detector to carry out the following operations:
(a) acquiring a plurality of background images related to non-uniformity of the grating system from all viewing angles by an imaging process without the object in place;
(b) acquiring a plurality of raw projection images from all viewing angles of the object by differential phase contrast (DPC) imaging process that uses the x-ray source, the detector, and the grating system to acquire a plurality of intensity images from which the plurality of raw projection images are derived;
(c) acquiring a plurality of corrected projection images from all viewing angles of the object comprising calculating each corrected projection image by removing a background image of the pluralities of background images from a raw projection image of the plurality of raw projection images at each view angle of all view angles;
(d) performing a three-dimensional (3D) computed tomography reconstruction of the object using the plurality of corrected projection images from all view angles; and
a display facility configured to display images of the object derived from the three-dimensional (3D) computed tomography reconstruction.

29. The system of claim 28, wherein the computer is further configured to carry out the following operation: computing a DPC image from the moire pattern.

30. The system of claim 28, wherein the computer is further configured to carry out the following operation: computing an attenuation image from the moire pattern.

31. The system of claim 28, wherein the computer is further configured to carry out the following operation: computing a dark-field image from the moire pattern.

32. The system of claim 28, wherein the computer is further configured to cause the source, detector, and grating system, to carry out the following operations:
  imaging the object with a second imaging process different from the imaging process of operations (a)-(d) to determine a region of interest in the object; and
  positioning the object so that the region of interest is positioned for operations (b)-(d).

33. The system of claim 32, wherein the second imaging process is computed tomography.

34. The system of claim 33, wherein the computed tomography is cone-beam computed tomography.

35. A system for imaging an object at an object position, the system comprising:
  an x-ray source of an imaging beam;
  an imaging detector in a path of the imaging beam;
  a grating system comprising:
    a steppable source grating between the x-ray source and the object position;
    wherein the steppable source grating is configured to step along the imaging beam during imaging; and
    a phase grating and an analyzer grating between the object position and the imaging detector;
  a gantry configured to rotate the x-ray source, the imaging detector, and the grating system about the object position;
  a computer system configured to control at least the x-ray source, the imaging detector, and the grating system to:
    (a) obtain a plurality of background images acquired at different view angles relevant to gantry rotation without the object at the object position;
    (b) acquire a plurality of raw projection images of the object at different view angles relevant to gantry rotation by a differential phase contrast (DPC) imaging process using the x-ray source, the imaging detector, and the grating system;
    (c) acquire a plurality of corrected projection images by using the plurality of background images to diminish background effects on the plurality of raw projection images; and
    (d) perform a three-dimensional (3D) computed tomography (CT) reconstruction of the object using the plurality of corrected projection images; and
  a display facility configured to display images of the object derived from the three-dimensional (3D) computed tomography (CT) reconstruction.

36. The system of claim 35, in which the steppable source grating comprises plural individual gratings sequentially placed in a path of the imaging beam for acquiring said plurality of raw projection images.

37. The system of claim 35, in which the computer system is further configured to acquire the plurality of raw projection images by rotating the gantry in a succession of subscans, wherein the steppable source grating presents a different grating parameter to the imaging beam for each subscan.

38. The system of claim 37, in which the different grating parameter is a different spacing between the steppable source grating and the x-ray source.

39. The system of claim 35, in which the x-ray source comprises an x-ray tube that has a focal spot size 0.05-2 mm and is operated at 10-150 kVp, the imaging detector has pixel size of 10-1000 μm and frame rate of 0.5-1000 fps, and the system spatial resolution is 2.5-25 lp/mm.

40. The system of claim 35, in which the spatial resolution of the system approaches 25 lp/mm.

41. The system of claim 35, in which the steppable source grating has a 30-200 μm grating pitch, and the phase grating has a 2-8 μm grating pitch.

42. The system of claim 35, in which the steppable source grating has a line width less than 50 μm.

43. The system of claim 35, further including a subsystem configured to acquire and display images of the object by a computed tomography imaging process other than said differential phase contrast (DPC) imaging process.

44. The system of claim 43, in which the subsystem comprises a second source emitting a second imaging beam and mounted on said gantry.

45. The system of claim 35, in which the computer system comprises a storage facility containing a plurality of background images acquired previously by an imaging process that includes rotating the x-ray source, the grating system, and the imaging detector about the object position.

46. The system of claim 35, in which the computer system is configured to acquire a plurality of the raw projection images for said three-dimensional (3D) computed tomography (CT) reconstruction of an object that is a patient's breast at spatial resolution of approximately 75-100 μm at a radiation dose that is less than for two-view standard screening mammography.

47. The system of claim 35, in which the computer system is configured to acquire the plurality of raw projection images for said three-dimensional (3D) computed tomography (CT) reconstruction of an object that is a patient's breast at spatial resolution of approximately 20-50 μm at a radiation dose equivalent to standard diagnostic mammography.

48. The system of claim 47, in which the radiation dose is approximately 6 mGy.

49. A system for imaging an object at an object position, the system comprising:
  an x-ray source of an imaging beam;
  an imaging detector in a path of the imaging beam;
  a grating system comprising:
    a source grating between the x-ray source and the object position; and
    a phase grating and an analyzer grating between the object position and the imaging detector;
    wherein the phase grating and the analyzer grating are misaligned to produce a moire pattern at the imaging detector;
  a gantry configured to rotate the x-ray source, the imaging detector, and the grating system about the object position;
  a computer system configured to control at least the x-ray source, the imaging detector, and the grating system to:
    (a) obtain a plurality of background images acquired at different view angles relative to gantry rotation without the object at the object position;
    (b) acquire a plurality of raw projection images of the object at different view angles relative to gantry rotation by a differential phase contrast (DPC) imaging process using the x-ray source, the imaging detector, and the grating system;

(c) acquire a plurality of corrected projection images by using the a plurality of background images to diminish background effects on the plurality of raw projection images; and (d) perform a three-dimensional (3D) computed tomography (CT) reconstruction of the object using the plurality of corrected projection images; and a display facility configured to display images of the object derived from the three-dimensional (3D) computed tomography (CT) reconstruction.

50. The system of claim 49, further including a subsystem configured to acquire and display images of the object by a second computed tomography imaging process different from said differential phase contrast (DPC) imaging process.

51. The system of claim 50, in which the subsystem comprises a CBCT source of imaging radiation and a CBCT detector that are mounted on said gantry for rotation about the object.

52. The system of claim 49, in which the computer system comprises storage containing a plurality of background images acquired previously by an imaging process that includes rotating the x-ray source, the grating system, and the imaging detector about the object position, and is configured to obtain said plurality of background images from said storage.

* * * * *